United States Patent [19]
Danielson

[11] Patent Number: 6,157,037
[45] Date of Patent: Dec. 5, 2000

[54] SENSING DEVICE AND METHOD FOR MEASURING EMISSION TIME DELAY DURING IRRADIATION OF TARGETED SAMPLES

[75] Inventor: J. D. Sheldon Danielson, Boulder, Colo.

[73] Assignee: PhotoSense, LLC, Boulder, Colo.

[21] Appl. No.: 09/205,755

[22] Filed: Dec. 4, 1998

[51] Int. Cl.$^7$ .................................................. G01N 21/64
[52] U.S. Cl. ................................... 250/458.1; 250/459.1; 356/318
[58] Field of Search ............................. 250/458.1, 459.1, 250/461.1; 356/318, 417; 436/172

[56] References Cited

U.S. PATENT DOCUMENTS

| | | | |
|---|---|---|---|
| 4,716,363 | 12/1987 | Dukes et al. | 324/77 |
| 4,840,485 | 6/1989 | Gratton | 356/317 |
| 4,845,368 | 7/1989 | Demas et al. | 250/459.1 |
| 5,196,709 | 3/1993 | Berndt et al. | 250/458.1 |
| 5,212,386 | 5/1993 | Gratton et al. | 250/458.1 |
| 5,257,202 | 10/1993 | Fedderson et al. | 364/498 |
| 5,317,162 | 5/1994 | Pinsky et al. | 250/461.2 |
| 5,424,843 | 6/1995 | Tromberg et al. | 356/442 |
| 5,462,879 | 10/1995 | Bentson | 436/136 |
| 5,485,530 | 1/1996 | Lakowicz et al. | 382/191 |
| 5,495,850 | 3/1996 | Zuckerman | 128/634 |
| 5,504,337 | 4/1996 | Lakowicz et al. | 250/461.2 |
| 5,515,864 | 5/1996 | Zuckerman et al. | 128/633 |
| 5,610,716 | 3/1997 | Sorin et al. | 356/357 |
| 5,624,847 | 4/1997 | Lakowitz et al. | 436/68 |
| 5,626,134 | 5/1997 | Zuckerman | 128/633 |
| 5,633,712 | 5/1997 | Venkatesh et al. | 356/345 |
| 5,646,734 | 7/1997 | Venkatesh et al. | 356/382 |
| 5,671,301 | 9/1997 | Kupershmidt | 385/1 |
| 5,757,013 | 5/1998 | Groger et al. | 250/458.1 |
| 5,818,582 | 10/1998 | Fernandez et al. | 356/318 |

OTHER PUBLICATIONS

A closed loop scheme for phase–sensitive flurometry, Apr. 14, 1995, Venkatesh Vadde and Vivek Strinivas, Indian Institute of Science, Department of Electrical Communication Engineering, Bangalore, India pp. 1–5.

Digital parallel acquisition in frequency domain florimetry, Sep., 1989, Brett A Federson, David W. Piston, and Enrico Gratton, Department of Physics, University of Illinois at Urbana–Champaign, Urbana, Illinois pp. 1–8.

*Primary Examiner*—Seungsook Ham
*Assistant Examiner*—Richard Hanig
*Attorney, Agent, or Firm*—John L. Isaac; Isaac & Associates

[57] ABSTRACT

An apparatus for measuring emission time delay during irradiation of targeted samples by utilizing digital signal processing to determine the emission phase shift caused by the sample is disclosed. The apparatus includes a source of electromagnetic radiation adapted to irradiate a target sample. A mechanism generates first and second digital input signals of known frequencies with a known phase relationship, and a device then converts the first and second digital input signals to analog sinusoidal signals. An element is provided to direct the first input signal to the electromagnetic radiation source to modulate the source by the frequency thereof to irradiate the target sample and generate a target sample emission. A device detects the target sample emission and produces a corresponding first output signal having a phase shift relative to the phase of the first input signal, the phase shift being caused by the irradiation time delay in the sample. A member produces a known phase shift in the second input signal to create a second output signal. A mechanism is then provided for converting each of the first and second analog output signals to digital signals. A mixer receives the first and second digital output signals and compares the signal phase relationship therebetween to produce a signal indicative of the change in phase relationship between the first and second output signals caused by the target sample emission. Finally, a feedback arrangement alters the phase of the second input signal based on the mixer signal to ultimately place the first and second output signals in quadrature. Mechanisms for enhancing this phase comparison and adjustment technique are also disclosed.

26 Claims, 6 Drawing Sheets

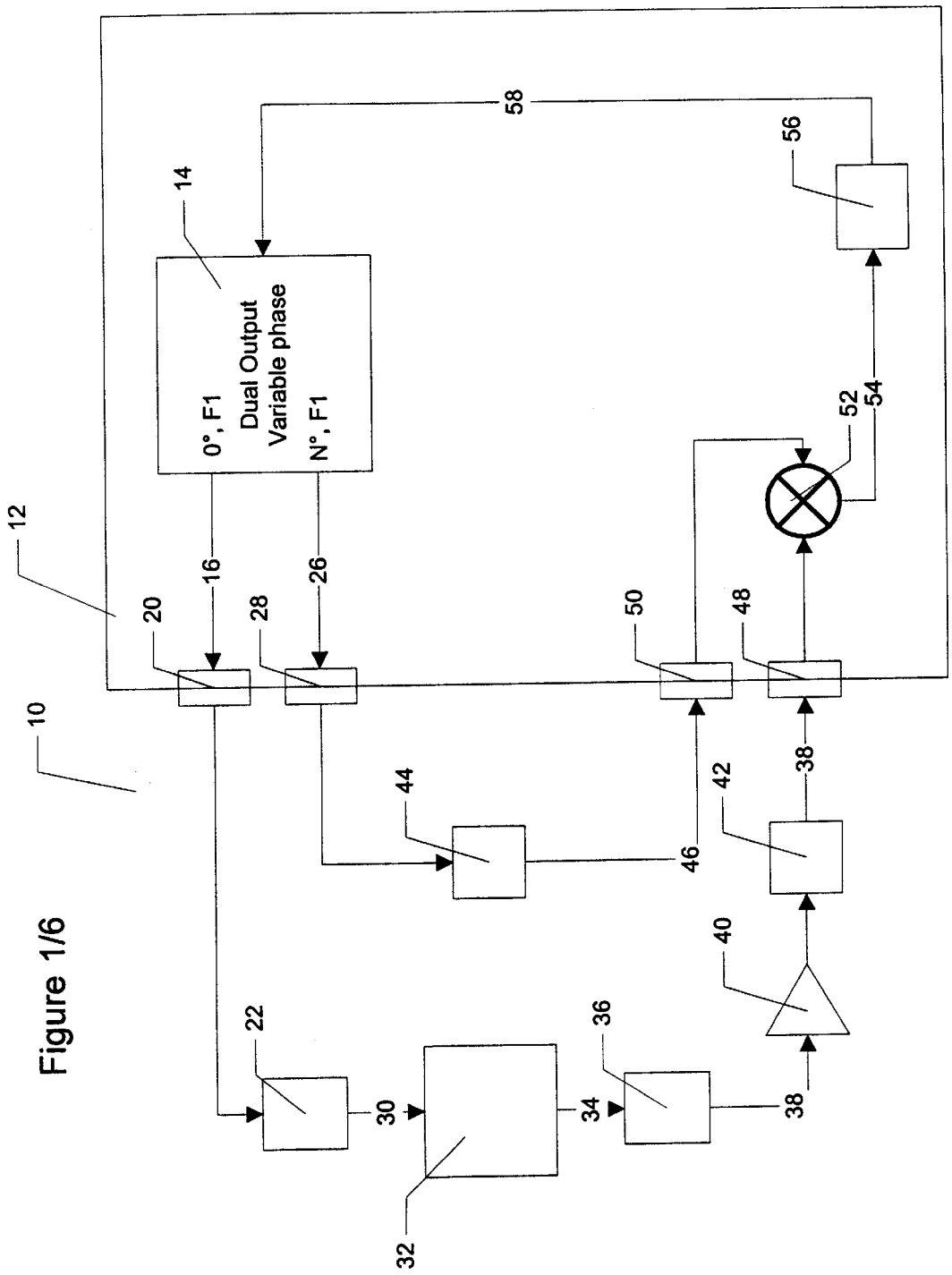
Figure 1/6

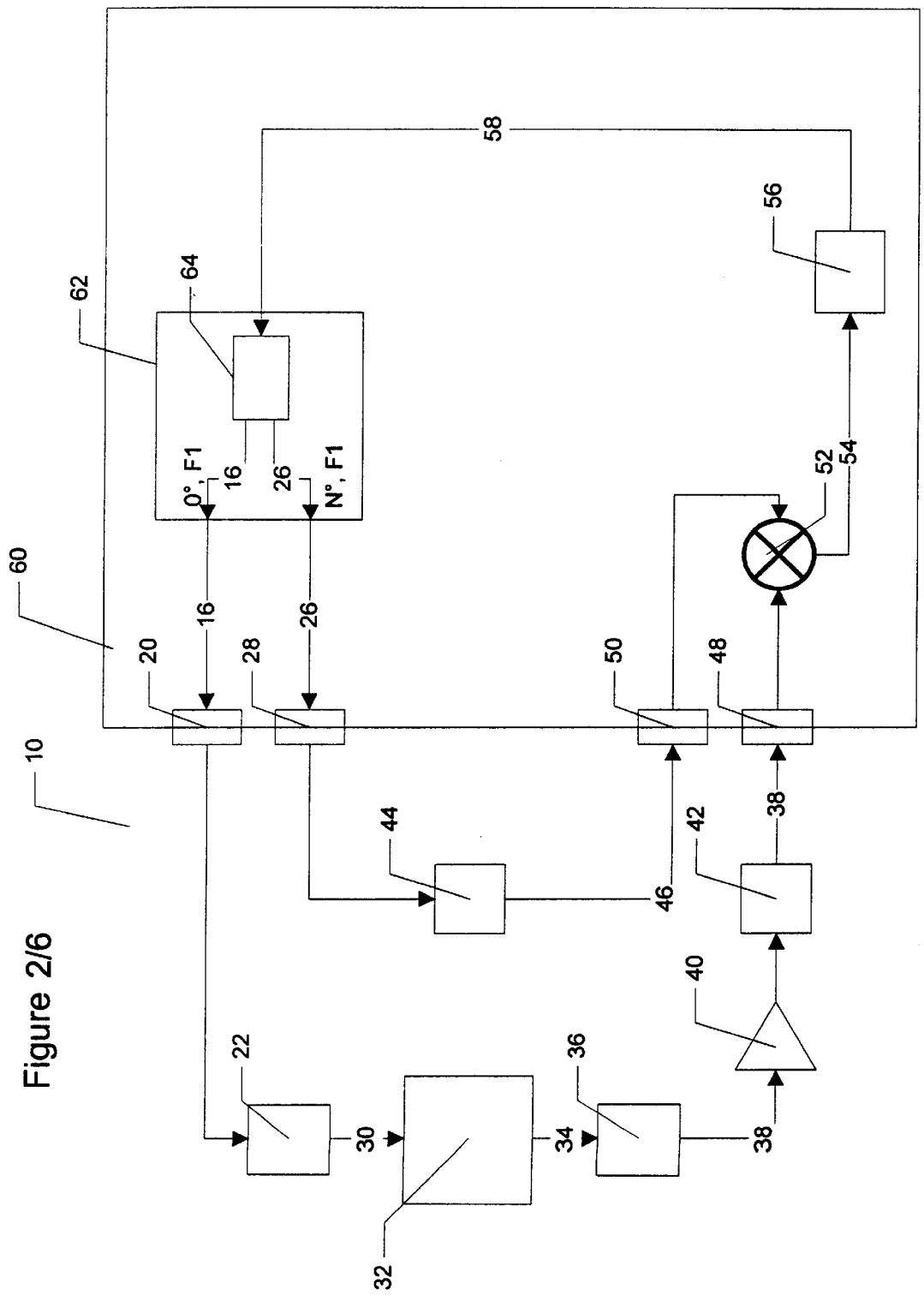
Figure 2/6

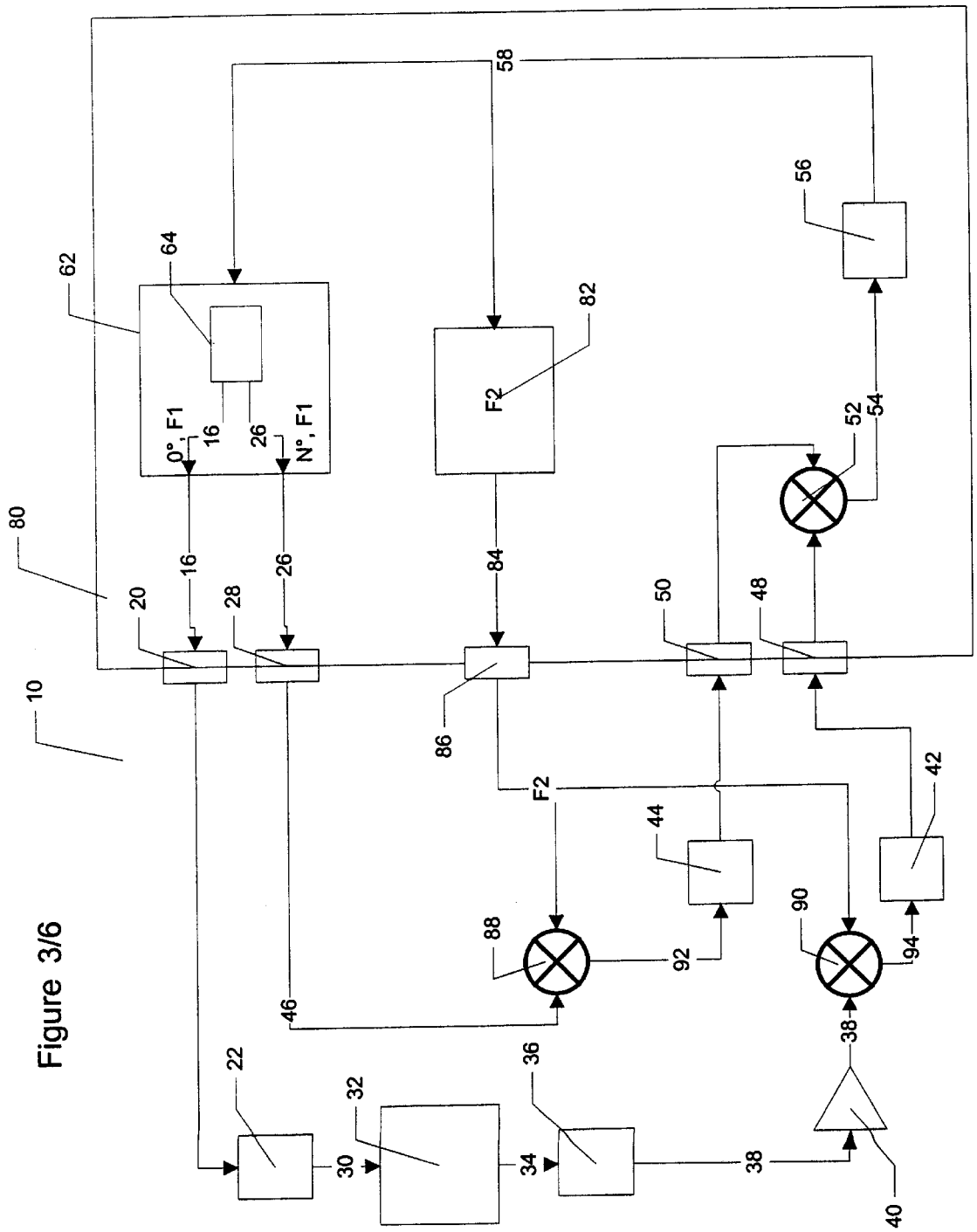
Figure 3/6

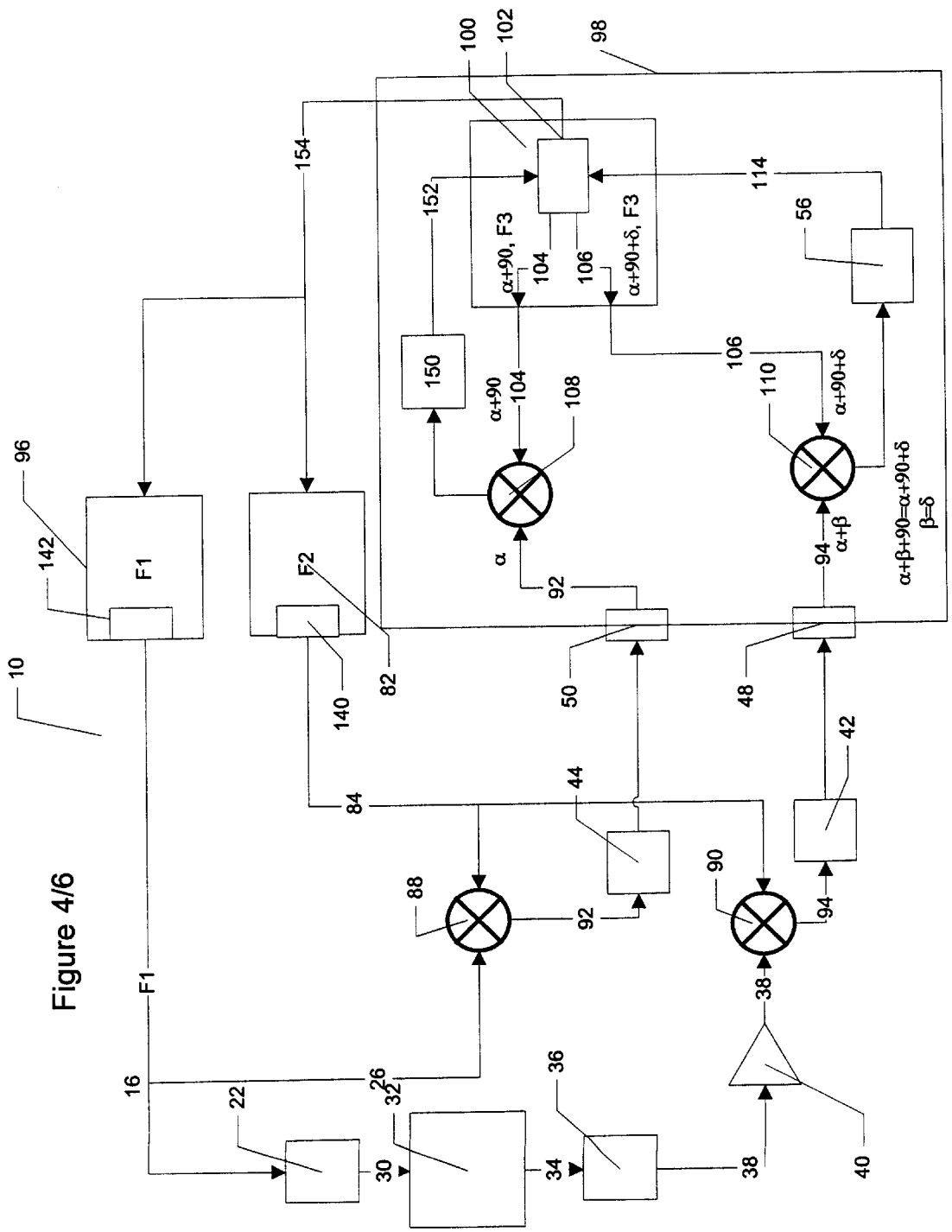
Figure 4/6

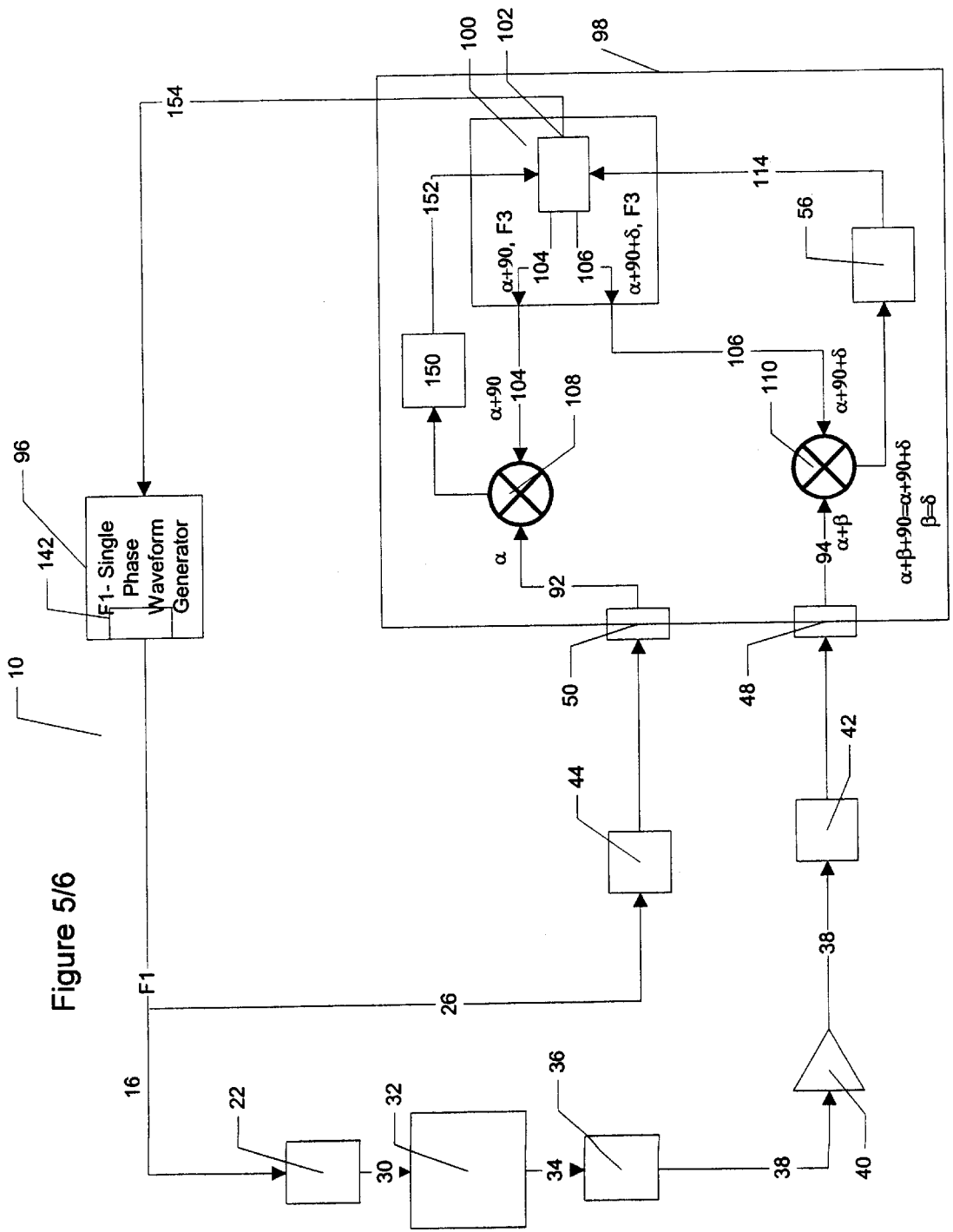

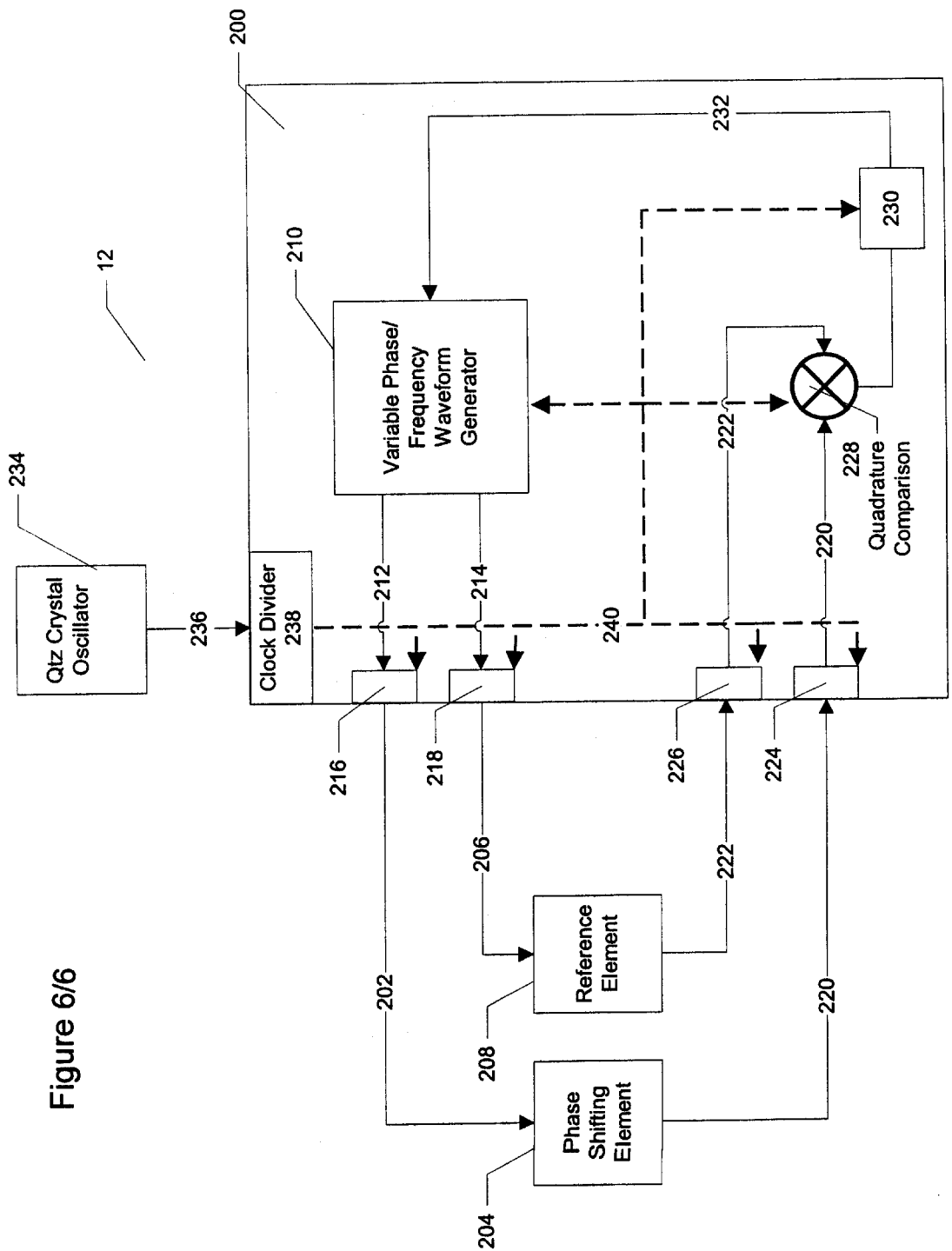
Figure 6/6

SENSING DEVICE AND METHOD FOR MEASURING EMISSION TIME DELAY DURING IRRADIATION OF TARGETED SAMPLES

CONTRACTUAL ORIGIN OF THE INVENTION

This invention was made with U.S. Government support under contract NAS9-97080 awarded by NASA and contract F33615-97-0729 awarded by the Department of the Air Force. The Government has certain rights in this invention.

BACKGROUND OF THE INVENTION

1. Field of the Invention

This invention relates generally to sensing instruments and methods for measuring the concentration of an analyte in a medium and, more particularly, to a device and method for measuring such concentrations by measuring the emission time delay during irradiation of a targeted sample surrounded by the analyte. Specifically, the present invention relates to a device and method for measuring exponential time constants, phase shifts, time delays and parameters derivable therefrom caused by irradiation of a targeted sample utilizing digital signal processing and especially luminescence quenching systems, phase shifts through networks, and time delays of photon migration through media.

2. Description of the Prior Art

Dynamic phase modulation, quenched luminescence sensors are well known. Instruments of this type have been, for example, developed or proposed for use in hospitals to monitor the concentration of gases such as oxygen, ionized hydrogen and carbon dioxide within the blood of patients. The particular substance of interest, for example oxygen, is known as the analyte.

As is known in the art, luminescence materials absorb energy and are driven from their ground state energy level to an excited state energy level in response to the application of energy from an electromagnetic radiation source such as light. These materials are unstable in their excited states, and they luminesce or give off excess energy as they return to their ground state. For example, the short wavelength ultraviolet light of black light stimulates dyes in a colored fabric to emit longer wavelengths, such as blue, green or red, and thus fluoresce. For the purposes of the present disclosure, the term "luminescence" as used herein is a general term which describes both fluorescence and phosphorescence, for all three terms are frequently used interchangeably in the art. The distinction and overlap of the terms is obvious to one skilled in the art.

In the presence of certain chemicals, many fluorescent materials are said to be quenched, i.e. the time constant of the fluorescence emission is altered by the effects of the surrounding chemicals. The degree of quenching of the fluorescence in turn can be related to the concentration of the quencher, which for example may be a chemical dissolved in water or mixed in air, such as oxygen in the blood of patients as explained above. There is a substantial amount of literature that describes fluorescent molecules that are selectively quenched by oxygen, carbon dioxide, glucose, pH, $NH_3$, metal ions, temperature and other environmentally and medically important analytes. These analytes are relevant to applications such as monitoring drinking water quality, industrial process control, monitoring of human respiratory function, human blood analysis for critical care patients, and the like.

One of the obstacles to the commercialization of fluorescence sensing devices has been a lack of inexpensive yet accurate instrumentation for the measurement of changes in the fluorescent time constant. For example, U.S. Pat. Nos. 4,845,368, 5,257,202, 5,495,850, 5,515,864 and 5,626,134 all disclose devices for measuring analyte concentration levels based on fluorescence. However, these particular devices are generally expensive and complicated.

The fluorescence lifetime or time constant, $\tau$, is the amount of time it takes the fluorescence emission to decrease by a factor of 1/e or about 63% after termination of irradiation as disclosed in U.S. Pat. No. 4,716,3632 by Dukes et al, in column 1, lines 37–41. This is common knowledge and is available in the literature reference, i.e. "Topics in Fluorescence Vol. 2—Principles", ed. Joseph Lakowicz. If light modulated sinusoidally at a frequency, f, is thus applied to the fluorescence sensor, the output is a sinusoidal emission of identical frequency, but having a phase shift and reduced amplitude with respect to the excitation signal. The equation governing the relationship between modulation frequency, f, phase shift, $\theta$, and the fluorescent time constant, $\tau$, is as follows:

$$\tau = \frac{\tan\theta}{2\pi f} \quad \text{or} \quad \theta \arctan(2\pi f \tau) \qquad \text{(Equation 1)}$$

Thus, if we know the excitation modulation frequency and can measure the phase shift of the emission signal relative to the excitation signal, we can determine the fluorescence constant, $\tau$, using the above Equation 1. In a fluorescence-based sensor, the fluorescence time constant is measured since this fluorescence time constant is altered by the presence of certain chemical species. Consequently, the concentration of chemical species can be determined by measuring the fluorescence time constant by measuring the phase shift associated therewith.

According to Equation 1, in order to measure the fluorescence time constant, one must know the excitation modulation frequency, f, and the phase shift of the light through the fluorescence system. With these quantities, the fluorescence time constant can be calculated and then related to analyte concentration. There are several different known techniques for determining the excitation frequency and phase shift of a system with an unknown time constant. One manner of determining this is by exciting the sample with a fixed frequency signal and then measuring the phase shift that results, that is the sample excitation modulation frequency is maintained constant while the signal phase, which varies with analyte concentration, is measured. U.S. Pat. Nos. 5,317,162, 5,462,879, 5,485,530 and 5,504,337 all disclose such fixed frequency, variable phase techniques and devices. Of particular interest is an article by Venkatesh Vadde and Vivek Srinivas entitled, "A closed loop scheme for phase-sensitive fluorometry", the American Institute of Physics, Rev. Sci. Instrum., Vol. 66, No. 7, July 1995, p. 3750.

Another principal way of conducting the above measurements is by exciting the sample with a modulation frequency that maintains a constant phase relationship between the excitation signal and the emission signal, that is the excitation frequency is varied in order to maintain a particular phase relationship. Such devices and techniques are known as phase-modulation, fluorescence-based sensing devices and are clearly illustrated in U.S. Pat. Nos. 4,840,485, 5,196,709, and 5,212,386, and in an article by Brett A. Feddersen, et al. entitled, "Digital parallel acquisition in frequency domain fluorimetry", American Institute of Physics, Rev. Sci. Instrum., Vol. 60, No. 9, September 1989, p. 2929. Of particular interest is U.S. Pat. No. 4,716,3632 by Dukes et al., which describes a feedback system that provides the modulation frequency required to give a constant phase shift of about 45°. The resulting frequency is then used to determine the analyte concentration which is a function of excited state lifetime.

U.S. Pat. No. 5,818,582 teaches the use of a DSP for fluorescence lifetime measurements, though not using quadrature signal comparison for determination of fluorescent sample phase shifts.

Despite the availability of the above-discussed techniques and sensing devices, there is a continuing need for improved fluorescence-based sensing instruments. In particular, there is a need for such devices which are useful for a broad range of applications involving exponential decay and time delay measurements, which are made from inexpensive components, and which present measurements in real time without the need for off-line signal processing as is the case of the patents to Federson, Gratton and others. A major detriment to many of the devices presently available is that they are very expensive to acquire and maintain. Moreover, analog systems of the present art are subject to drift and therefore unnecessary errors. Such systems should be, to the contrary, inexpensive, convenient to use and provide adequate sensitivity over an extended and continuous measurement range. The system of the Dukes patent emphasizes optimal sensitivity over a wide measurement range, but in so doing, requires very complex and expensive system components. To the contrary, optimal sensitivity can be sacrificed for sub-optimal, adequate sensitivity in order to achieve inexpensive, less complicated measurement techniques. In addition, the measurement approach of such devices should be susceptible to convenient and precise readout.

SUMMARY OF THE INVENTION

Accordingly, it is one object of the present invention to provide an apparatus and method for measuring emission time delay during irradiation of targeted samples.

It is another object of the present invention to provide sensing instruments which are applicable to a broad range time delay, phase shift and exponential decay measurements involving luminescent materials and various scattering media.

Yet another object of the present invention is to provide fluorescence-based sensing instruments which are made from inexpensive components.

Still another object of the present invention is to provide an apparatus and method for measuring emission time delay during irradiation of targeted samples utilizing digital signal processing to determine the emission phase shift caused by the sample.

A further object of the present invention is to provide an apparatus and method for measuring luminescence-quenching systems, specifically oxygen sensitive systems.

To achieve the foregoing and other objects and in accordance with the purpose of the present invention, as embodied and broadly described herein, an apparatus is disclosed for measuring emission time delay during irradiation of targeted samples by utilizing digital signal processing to determine the emission phase shift caused by the sample. The apparatus includes a source of electromagnetic radiation adapted to irradiate a target sample. A mechanism generates first and second digital input signals of known frequencies with a known variable phase relationship, and a device then converts the first and second digital input signals to analog sinusoidal signals. An element is provided to direct the first input signal to the electromagnetic radiation source to modulate the source by the frequency thereof to irradiate the target sample and generate a target sample emission. A device detects the target sample emission and produces a corresponding first output signal having a phase shift relative to the phase of the first input signal, the phase shift being caused by the emission time delay in the sample. A member produces a known phase shift in the second input signal to create a second output signal. A mechanism is then provided for converting each of the first and second analog output signals to digital signals. A mixer receives the first and second digital output signals and compares the signal phase relationship therebetween to produce a signal indicative of the change in phase relationship between the first and second output signals caused by the target sample emission. Finally, a feedback arrangement alters the phase of the second input signal based on the mixer signal to ultimately place the first and second output signals in quadrature. Mechanisms for enhancing this phase comparison and adjustment technique are also disclosed.

BRIEF DESCRIPTION OF THE DRAWINGS

The accompanying drawings which are incorporated in and form a part of the specification illustrate preferred embodiments of the present invention and, together with a description, serve to explain the principles of the invention. In the drawings:

FIG. 1 is a schematic illustrating an embodiment of the present invention utilizing a direct phase adjustment, constant frequency technique with digital signal processing for measuring emission phase shift to determine time delay through an irradiated sample.

FIG. 2 is a schematic illustrating another embodiment of the present invention utilizing variable-frequency and variable-phase techniques for measuring emission phase shift to determine time delay through an irradiated sample.

FIG. 3 is a schematic illustrating yet another embodiment of the present invention similar to that of FIG. 2 but incorporating signal down conversion steps.

FIG. 4 is a schematic illustrating yet another embodiment of the present invention similar to that of FIG. 3 but incorporating dual quadrature signal down conversion steps.

FIG. 5 is a schematic illustrating yet another embodiment of the present invention similar to that of FIG. 4 but eliminating the means for the downconverting of high frequency signals to lower frequencies for quadrature phase detection.

FIG. 6 is a schematic illustrating yet another embodiment of the present invention using a single analog timing element and a DSP for real time determination of phase and lifetime.

DETAILED DESCRIPTION OF THE PREFERRED EMBODIMENTS

Referring initially to FIG. 1, a closed-loop lifetime measurement device 10 is illustrated which incorporates a Digital Signal Processor (DSP) 12. Venkatesh and Srinivas, in the prior art references discussed above, disclose a closed-loop fluorescent-decay time measurement system that allows a phase demodulator to operate in an optimal null condition. This is accomplished using two analog timing elements including a crystal-controlled frequency generator and a second analog timing element to vary the phase of a measurement reference signal so that signals to the demodulator are always in quadrature. An important aspect of this disclosed technique is that the reference channel is phase advanced in order to maintain quadrature at the phase demodulator.

Within the DSP 12 of FIG. 1, all the components referred to below are digital and defined by software loaded into the DSP chip. In the DSP 12, a constant frequency, dual-output, variable-phase waveform generator 14 is provided and adapted to generate a first experimental digital signal 16 and a second reference digital signal 26. The digital signals 16, 26 are preferably identical in frequency. The experimental signal 16 is directed through a digital-to-analog converter 20 where it is converted into an analog signal which drives an electromagnetic radiation-emitting device 22. The dual-output, variable-phase waveform generator 14 causes the reference signal 26 to be phase advanced a known number of degrees (N°) relative to experimental signal 16. Reference signal 26 is then directed through a second digital-to-analog converter 28.

In preferred form, the device 22 is a light emitting diode (LED). The device 22 is activated by the analog form of the signal 16 and generates a light emission 30. The emission 30 is directed to a target sample 32 which includes therein material which will emit energy 34 as a result of being impinged by the light 30. In one preferred form of the invention, the target sample 32 is a fluorescent material designed to generate a fluorescence emission 34 upon contact with the LED emission 30. However, it should be understood that the target sample 32 may include any appropriate emission-delay generating system as discussed above.

The emissions 34 are detected by a device 36, which in preferred form is a photodiode. The detection device 36 then generates an output signal 38 which has a frequency identical to the experimental signal 16 but is phase retarded as a result of the time delay imposed by the target sample 32. Thus, the output signal 38 is now phase-shifted an unknown amount relative to the experimental signal 16 and the reference signal 26. In preferred form, the output signal 38 is directed through a pre-amplifier 40. A pair of anti-aliasing filters 42, 44 are provided, and the output signal 38 passes through the filter 42 while the reference signal 26 passes through the filter 44, thereby becoming output reference signal 46. Thus, both the experimental signal 16 and reference signal 26 are effectively treated substantially identically outside the DSP 12 except for the phase shift resulting from the target sample 32. This is due to the fact that while the LED 22, the photodiode 36 and the pre-amplifier 40 all add phase shifts to the experimental signal 16 that do not exist in the reference signal 26 chain, these shifts, though significant, are calibrated out. In the preferred embodiment, the phase shift caused by LED 22, the photodiode 36 and the pre-amplifier 40 is negligible compared to the phase shift caused by anti-aliasing filters 42 and 44. The system 10 uses duplicate anti-aliasing filters 42, 44 to eliminate major phase imbalances that would otherwise exist in the two channels. Both signals 38 and 46 are passed through respective analog-to-digital converters 48, 50 to create counterpart digital output signals within the DSP 12.

The output reference signal 46 is then mixed with the output experimental signal 38 at the signal mixing device 52, which in this particular embodiment is preferably a phase demodulator. As was previously stated, the original reference signal 26 is phase-shifted by the digital waveform generator 14 a specific number of degrees so that the experimental input signal 16 and the reference input signal 26 are out-of-phase by a known, predetermined amount. However, due to the phase shift imposed by the target sample 32, the phase differences between the output signals 38 and 46 at the mixing member 52 are unknown. Therefore and in preferred form, the phase demodulator 52 indicates when the reference signal 46 (A) relative to the experimental signal 38 (B) are in quadrature, or 90° apart. In other words, 90°−B=A if the signals are in quadrature. If the signals 38 and 46 are in fact in quadrature, then no changes are made to the relative phase offset between input signals 16 and 26. However, due to the phase shift caused by the target sample 32, the signals 38 and 46 are not initially in quadrature at 52.

As a result, the phase demodulator 52 generates a signal 54 comprised of both AC and DC components, the DC component represents the phase difference between the signals 38 and 46 relative to 90°. This signal 54 is preferably passed through a low pass filter 56 to remove the AC component creating a DC error signal 58. The sign and magnitude of the DC error signal 58 indicates the relative phase difference between input signals 38 and 46 and is preferably zero when the input signals 38 and 46 are in quadrature. Based on the error signal 58, the digital waveform generator 14 continuously modifies the phase advance (N°) of the reference signal 26. In this manner, the device 10 continues to change the relative phase of the signals 16 and 26 until the phases of the output experimental signal 38 and the output reference signal 46 are in quadrature at the phase demodulator 52, at which point error signal 58 is substantially zero. At this stage, the phase shift through the sample 32 is 90°−N°, with N° being the phase advance of the signal 26 relative to signal 16. This phase shift quantity is then utilized with the known frequency of the experimental signal 16 and Equation 1 to calculate the lifetime of the target sample 32, which in turn will provide the desired information about the analyte surrounding the target sample 32 as discussed above.

One of the important aspects of the embodiment illustrated in FIG. 1 is that this embodiment utilizes parallel analog paths for both the reference and experimental signals in combination with digital processing. These parallel paths are used for two principal reasons. The first is that the digital-to-analog converters 20, 28 as well as the analog-to-digital converters 48, 50 introduce time delays into the signals passing through them. Any difference in time delay between the two paths will result in an undesired phase-offset between them. However, if both of the experimental and reference signals 16, 26 pass through matched identical converters 20, 28 and 48, 50, the reconstruction and digitization will not result in a relative time delay of one signal with respect to the other.

The second reason is that the anti-aliasing filter 42 introduces a significant amount of phase lag into the experimental analog signal 38, i.e. about 26 degrees at 20 kHz. By passing the reference analog signal 26 through an identical anti-aliasing filter 44, the phase lag as a result of the anti-aliasing filter is canceled. Additionally, any drift in phase cause by the anti-aliasing filter 42 in the experimental signal path 38 will tend to be canceled by similar drift in the anti-aliasing filter in the reference signal path 26. The symmetrical treatment of the experimental 38 and reference 46 signals means that the phase difference between them is due only to the phase delay resulting from the target sample 32 as well as the known phase advance created by the digital phase shifter 24. While the LED driver circuit, the LED, the photodiode and the preamplifier all contribute small phase shifts in the experimental signal 16 that are not cancelled by similar components in the reference signal 26 path, these phase shifts are cancelled in other ways as indicated above. In addition, since all operations within the DSP 12 are digital calculations, they are free from any drift or non-linearity whatsoever.

In the above embodiment of FIG. 1, the DSP 12 implementation of the device 10 utilizes only one analog timing element for the generation of the reference and experimental signals 26, 16, for the basic phase shifting of the reference signal 26, and for the phase demodulation of signals 46 and 38 at the demodulator 52. The time base for the DSP frequency generation and the phase shifting is preferably derived from a single external crystal oscillator. Moreover, the phase shifting of the reference signal 26 is preferably accomplished by the addition of two 32-bit numbers which does not introduce a phase jitter as is true of pure analog systems or of systems using more than one analog timing element for signal generation, comparison and phase shifting. As a result of the lack of phase jitter or instability (drift) between the two signals 16, 26, extremely small phase changes, e.g. 0.001 degrees, caused by the target sample 32 are detectable by the device 10. Moreover, the advantage of using identical anti-aliasing filters 42, 44 is that any changes in the filter properties resulting from changing temperatures are reflected in both the experimental and reference signal paths and are therefore canceled. This substantially reduces electronic phase drift as compared to prior art devices.

As was discussed above, existing devices also utilize changes in frequency, rather than phase, to measure fluorescence emissions or the like. In particular, U.S. Pat. No. 4,716,363 by Dukes et al. describes a fluorescence lifetime measurement system that operates in this manner. In particular, the excitation frequency of Dukes is varied such that a constant predetermined phase shift is obtained through the fluorescence experiment. The predetermined phase shift is selected to achieve optimal sensitivity to changes in lifetime. Since the frequency is inversely proportional to the lifetime as illustrated above in Equation 1, the frequency can be directly related to the quencher or analyte concentration of the target sample 32 thereby circumventing the need to calculate lifetime or phase.

While this particular system of Dukes operates fine in certain instances, there are significant drawbacks. Without going into a detailed discussion of this reference, the Dukes' system operates such that the oscillator frequency is adjusted to maintain a fixed and optimum phase-shift through the fluorescence experiment. However, in sensing applications where the change in the lifetime of the fluorescent experiment is large, the frequency must change over an equally large range. Thus, if the lifetime changes by a factor of 100, then the oscillator must change frequency by a factor of 100. The use of smaller or larger phase-offsets will shift the maximum and minimum frequencies up and down but will not compress the required range. There are many situations where generating frequencies over such a wide range is impractical because it is prohibitively complex or expensive. As a result of this problem, the present invention provides the additional embodiments of the invention as illustrated in FIGS. 2–4.

Referring now in particular to FIG. 2, it should be understood that like components throughout all of the Figures and embodiments of the present invention will have like numerals and indicators. In this particular embodiment of FIG. 2, the device 10 includes a DSP 60. The DSP 60 preferably includes a dual-output, variable-phase waveform generator 62. Within the waveform generator 62 is a frequency and phase calculator 64 which determines the appropriate frequency and phase relationship of the two signals 16 and 26 output by generator 62. The frequency generator 62 generates an initial experimental signal 16 with a known phase and an initial reference signal 26 which is phase advanced relative to the experimental signal 16 by the calculator 64.

As with the prior embodiment of FIG. 1, the signals 16, 26 pass through their respective digital-to-analog converters 20, 28, and the experimental signal 16 activates an electromagnetic radiation emitting device 22 such as an LED. The emissions 30 impinge on the target sample 32 which in turn generates emissions 34 detected by the detection member 36 such as a photodiode, all being similar to the prior embodiment illustrated in FIG. 1. The experimental output signal 38 passes through a preamplifier 40, and both the experimental output signal 38 and the reference output signal 26 pass through respective anti-aliasing in filters 42, 44 and analog-to-digital converters 48, 50. As in the prior embodiment, the output signals 38, 46, in digital form, are then combined at the mixer 52. If the signals 38, 46 are not in quadrature, the DC component of the signal 54 is a number other than zero.

The AC component of signal 54 is removed by the low pass filter 56. The output of the filter 56 is a DC error signal 58, the sign and magnitude of which indicates the relative phase difference between signals 46 and 38. As explained previously, the DC error signal 58 is preferably zero when signals 38 and 46 are in quadrature. The DC error signal 58 output from the filter 56 is then directed back to the frequency calculator 64 within the waveform generator 62 to simultaneously control both the frequency and the phase of the output signals 16 and 26 as described below.

In this embodiment of FIG. 2, the feedback error signal 58 causes the waveform generator 62 to simultaneously change both the phase advance of the signal 26 relative to the signal 16 as well as the modulation frequency of both signals 16 and 26. The phase and modulation frequency are changed simultaneously until the DC error signal 58 indicates that input signals 46 and 38 are in quadrature, that is when the error signal 58 is substantially zero. The phase and frequencies of the waveforms determined by the calculator 64 are indicated by binary numbers stored in the DSP 60. Although the waveform generator 62 and the contained frequency and phase calculator 64 are digital, the high digital resolution affords effectively continuous changes in frequency and phase offset. Thus, when the DC error signal 58 is substantially zero, the time constant of the luminescence system can be calculated using Equation 1. The phase delay through the sample 32 is simply 90°−N° with N° being the phase advance of the signal 26, and the frequency is known from the digital number generated by the calculator 64.

The simultaneous and continuous variation of phase and frequency in a feedback loop acts to compress the phase and frequency ranges that are required for a particular luminescence lifetime range. Compared to the prior art techniques of Dukes and Venkatesh as disclosed above, this FIG. 2 embodiment of the invention uses less expensive, more convenient components that have narrower operating ranges. Moreover, while this embodiment of FIG. 2 of the present invention employs continual and simultaneous changes in phase offset and frequency of the output signals 16 and 26, thereby sacrificing optimum lifetime measurement sensitivity, a heretofore unanticipated result is the benefit of frequency and phase range compression for luminescence sensors.

This compression of the frequency and phase range over a wide lifetime range is accomplished by using the continuously variable phase offset and continuously variable frequency provided by the waveform generator 62. Since the phase offset of the dual-output, variable-phase oscillator 62 changes as the frequency changes, then a much smaller frequency range is needed. For example, if the phase-offset of the variable-phase oscillator 62 were to change by 0.0038 degrees per Hz, then the entire range between 1 μsec and 100 μsec can be covered with a frequency range of 19,900 Hz–3,900 Hz. This is a frequency range of only 5:1 as compared to a range of 100:1 required by prior art devices and techniques using variable frequency and a predetermined, fixed phase offset. Thus, in this particular embodiment illustrated in FIG. 2, both the phase and frequency may vary and is known as "phase compression", for the use of a continuously variable phase-offset compresses the frequency and phase ranges. This extends the measurable lifetime range for systems using inexpensive, limited range components including but not limited to oscillators, waveform generators, amplifiers, and analog-to-digital and digital-to-analog converters.

In the phase compression system 10 of FIG. 2, the frequency and phase output of the multiple phase oscillator 62 is determined by a DC error signal 58 derived from the mixer 52. The error signal 58 from the mixer 52 and low pass filter 56 controls the output frequency and phase of the oscillator 62 so that the two signals 38, 46 input to the mixer 52 are eventually in quadrature. This error signal 58 passes to the frequency and phase calculator 64 which determines how the frequency and phase should change based on the error signal 58. The outputs of the calculator 64 are binary numbers representing frequency and phase, and these numbers are used by the waveform generator 62 to generate a digital representation of two sine waves, 16 and 26, at the frequency and phase offset specified by the calculator 64.

While the waveform generator 62 creates a reference signal 26 that is advanced with respect to the experimental signal 16 as with the embodiment of FIG. 1, the difference in this embodiment of FIG. 2 is that the frequency of the signals 16 and 26 change continuously and simultaneously with changes in the phase offset. In one preferred embodiment, the calculator 64 changes the frequency and phase according to the following relationship:

$$N°=F \cdot CF + N_{base} \quad \text{Equation (2)}$$

where N° is the phase offset between signals 16 and 26, F is the frequency of signals 16 and 26, CF is the compression factor, and $N_{base}$ is the base phase offset.

For example with CF=0.0038 deg/Hz, $N_{base}$=6.18 deg and a luminescence sensor lifetime of 101.6 μsec, the calculator 64 adjusts the system frequency to 4000 Hz, and the phase offset to 21°. These are the conditions where the error signal 58 is substantially zero. With equivalent CF and $N_{base}$ parameters, and a luminescent sensor lifetime of 1.2 μsec, the calculator adjusts the system frequency to 19,900 Hz, and the phase offset to 82°. When the signals 38 and 46 are in quadrature, the lifetime of the sample 32 can be calculated using the known phase and frequency. Since the action of the calculator 64 compresses the frequency and phase range, inexpensive components with limited range can be used in the present invention in place of expensive and complex components.

In the above example, the frequency and phase range compression because the shortest lifetime to require a frequency of under 20,000 Hz. Currently, it is a distinct advantage to use DSP compatible analog-to-digital and digital-to-analog converters that have a maximum frequency range of 20,000 Hz. This is due to the fact that such limited frequency range components are mass produced for consumer audio applications and thus are inexpensive and simpler to use as compared to wider frequency range components produced for more limited markets, e.g. scientific instrumentation.

A third embodiment of the present invention incorporates the concept of down conversion by mixing the reference and experimental signals with another third signal of different phase and frequency, i.e. down converting, to a fixed or variable lower frequency while preserving relative phase information. In a simple lifetime measurement system embodiment as illustrated in FIG. 1 and FIG. 2, the frequency at which the exciting light 30 is modulated and the frequency at which phase measurement takes place in the DSP 12 are essentially identical. As higher modulation frequencies are demanded by the measurement of shorter fluorescent or luminescent lifetimes, a point is reached where the necessary program steps for phase comparison and correction cannot be executed between samples. This particular problem is overcome by the embodiments illustrated in FIGS. 3–4. In these embodiments, the high-frequency experimental and reference signals are each linearly multiplied by a local oscillator frequency in a mixer. The resulting waveform or signal is then filtered and presented to the analog-to-digital converter.

Referring now with particularity to FIG. 3, the device 10 includes a DSP 80 having a dual-output, variable-phase waveform generator 62. As in the prior embodiment, a frequency and phase calculator 64 determines the appropriate frequency and phase relationship of the two signals 16 and 26 output by generator 62. The experimental signal 16 and the reference signal 26 pass through their respective converters 20, 28. The signal 16 activates an LED 22 which generates an emission 30 to impinge target sample 32 to create an emission 34 which is detected by the photodiode 36. The output signal 38 passes through the pre-amplifier 40.

In this particular embodiment, a second frequency generator 82 is disposed within the DSP 80 and generates a signal 84 having a frequency different from the frequencies of the output signals 38, 46. The signal 84 passes through a digital-to-analog converter 86 and is then mixed with the output reference signal 46 at a mixer 88 as well as with the output experimental signal 38 at yet another mixer 90. When the signal 84 mixes with each of the signals 38, 46, a modified output reference signal 94 and a modified output experimental signal 92 are created, respectively. Each of the signals 92 and 94 passes through their respective anti-aliasing filters 44 and 42, and analog-to-digital converters 50, 48 and are then demodulated at the digital mixer 52.

When the signal 84 is mixed with the reference signal 46, both the sum and the difference frequencies are incorporated into the modified output signal 92. Likewise, both the sum and difference frequencies of the signal 84 and the signal 38 are reflected in the modified output signal 94. The anti-aliasing filters 42 and 44 preferably remove the sum frequency of the signals 84 and 46 and the sum frequency of the signals 84 and 38, respectively, so that only the difference frequency of the signals 84 and 46 and difference frequency of the signals 84 in 38 are mixed and compared at the mixer device 52. At the demodulator 52, the phases of the signals 92 and 94 are compared, and a feedback signal 54 is generated by the mixer 52. This feedback signal 54 passes through the low pass filter 56 and is then returned to the frequency and phase calculator 64. The signal 58 is also directed towards the second frequency generator 82. As in the prior embodiment, the error signal 58 indicates the sign and magnitude of the phase difference between signals 92 and 94, and is preferably zero when these signals are in quadrature. The calculator 64 simultaneously changes the phase and frequency of output signal 16 and 26, as in the prior embodiment of FIG. 2, such that a condition of quadrature is maintained at the mixer 52.

The difference frequencies of the modified output signals 92 and 94 are held constant by action of the error signal 58 on the second frequency generator 82. The second frequency generator 82 tracks the signal frequency output of the frequency generator 62 by always maintaining a signal frequency output that is different, i.e. higher or lower, by a constant value, for example 10 kHz. Constant frequency inputs to the demodulator 52 are preferred. One can anticipate a scheme, however, which sends variable frequency inputs to the demodulator 52 though there is generally no benefit to such an implementation.

In evaluating this embodiment of FIG. 3, when a sinusoid of one frequency linearly multiplies a sinusoid of another frequency, the resulting waveform or signal consists of a linear combination of a pair of sinusoids whose individual frequencies are the sum and difference of the two original frequencies. In a practical lifetime measurement circuit as in the embodiment of FIG. 3, the sum frequency is rejected by a filter, and the difference frequency which may be quite low is passed to the analog-to-digital converters for further processing within the DSP 80 as described above. The difference frequency can have any convenient value, and it is determined only by the relationship between the signals 38 and 46 frequency and the signal 84 frequency. The phase relationship between the high frequency reference signal 46 and the experimental signal 38 are maintained through the down conversion process.

Another embodiment of FIG. 3 uses external digital waveform generators in place of the component generators 62 and 82 and the D/A converters 20, 28 and 86. This particular embodiment would be used when the frequencies of the signals 16 and 26 are too high to be generated internally within digital signal processor 80. In this case the external generators would preferably consist of single chip waveform generators which would be controlled by the digital signal processor 80 and derive their clock frequency from the same analog oscillator as digital signal processor 80.

Referring now to FIG. 4, this embodiment imposes an additional requirement and capability on the down conversion process as compared to that of FIG. 3 explained above. As a part of measuring the phase difference between the experimental and reference signal sinusoids, the DSP of this FIG. 4 executes a program that implements an additional numerical direct digital synthesis frequency generator, the numerical direct digital synthesis generator being used in all the prior embodiments as the devices 14 and 64. Referring to FIG. 4, the down conversion arrangement of FIG. 3 remains substantially the same. However, the experimental signal 16 and the reference signal 26 are generated by one single-output frequency generator 96 and are generated at the same phase and frequency.

In one embodiment as illustrated in FIG. 4, the frequency generators 96 and 82 are specialized DSP components that are external to the main digital signal processor 98 and contain digital-to-analog converters 142 and 140, respectively. In another embodiment, the frequency generators 96 and 82 may be internal to the main DSP 98, as shown for example in FIGS. 1 and 2. While it is actually preferred that the frequency generator 96 is implemented internally within the DSP 98, one would then preferably then use the down-conversion single quad technique of FIG. 2. When the signals 92 and 94 in this embodiment of FIG. 4 pass through the analog-to-digital converters 50 and 48, they are not mixed directly together as with the prior embodiments. Instead, an additional dual output, multiphase digital synthesis frequency generator 100 is provided within the DSP 98.

In preferred form, the dual-output, multi-phase digital synthesis frequency generator 100 includes a frequency and phase calculator 102 that generates a first internal signal 104 and a second internal signal 106, each of which has a frequency which matches exactly the frequency of the signals 92 and 94, which is the difference frequency between the frequency generated by the generator 96 and the frequency generated by the generator 82. The first internal signal 104 is generated such that it has a phase relative to input signal 92 of 90°. This is accomplished by mixing the signals 92 and 104 at an internal mixer 108. The output of the mixer 108 is directed to a low pass filter 150 which outputs an error signal 152, the sign and magnitude of which indicates the relative phase difference between signals 104 and 92. The error signal 152, preferably zero when the signals 92 and 104 are in quadrature, is directed to the frequency and phase calculator 102. The calculator 102 then adjusts the phase of the signal 104 until the error signal 152 indicates that signals 92 and 104 are in quadrature.

At the same time, the signal 94 is directed toward another internal mixer 110, and the frequency generator 100 generates the second internal signal 106 of preferably identical frequency with the signals 92, 94 and 104, and with a phase that is advanced a known amount with respect to the phase of the signal 104. The signal 106 is mixed with the signal 94 at the internal mixer 110, the output of which is directed through a low pass filter 56 to create another internal error signal 114 which is directed to the frequency and phase calculator 102. Based on the sign and magnitude of the error signal 114, the phase of the signal 106 is shifted until the signal 106 and the signal 94 are in quadrature at the mixer 110. Since the signals 92 and 94 preferably differ in phase only based on the phase shift caused by the target sample 32, each of the signals 92 and 94 are individually placed into quadrature with separate signals in order to determine this difference in phase at the synthesis frequency generator 100. The phase difference between the signals 104 and 106 thus reflects the phase difference between the input signals 92 and 94. The fluorescence lifetime of the sample can be calculated using the measured phase shift and frequency with Equation 1.

In this embodiment of FIG. 4, the frequency generators 82 and 96 are inexpensive, small single integrated circuit, commercially available components. These external generators 82 and 96 do not, however, provide a means for communicating the current phase of the output signals 16 and 26 to the DSP 98. As a result, the digitized reference signal 92 is at some unknown phase. The additional internal phase lock loop, which is made up of the mixer 108, the filter 150, the frequency generator 100 and the frequency calculator 102, generates a signal 104 that is phase locked to the input signal 92. The signal 104 then becomes the phase reference for the second mixing process using mixer 110.

The following example illustrates the purpose and function of the additional phase locked loop of FIG. 4. The signal 92 is digitized at 50 and has some unknown phase which we designate "$\alpha$". Simultaneously, the signal 94 is digitized at 48 and differs in phase from the signal 92 by "$\beta$", the result of the phase shift caused by the sensor 32 and any phase shifts due to the analog components 22, 36 and 40. Thus, the signal 94 has a phase of α+β as indicated in FIG. 4. The phase locked loop which includes the mixer 108 generates the signal 104 with a phase shift of α+90°. The frequency generator 100 then creates a signal 106 that has an added phase shift of "δ" relative to the signal 104. Therefore, the signal 106 has a phase of α+90+δ. The mixer 110 and error signal 114 impose on the signal 106 the condition that it must be in quadrature with the signal 94. This is accomplished by adjusting δ, the amount of additional phase shift relative to signal 104. At the mixer 110 we find that the signals 94 and 106 differ by 90°, that is the phase of the signal 94 plus 90°, α+β+90, is equal to the phase of signal 106 which we know to be α+90+δ, or $$\alpha+\beta+90=\alpha+90+\delta.$$

Simplifying the above, we find that β=δ. The amount of known phase shift added to the signal 106, δ, is equal to the phase shift caused by the fluorescence experiment 32, along with the other analog components 22, 36, and 40. Finally the phase shift indicated by δ may be used with Equation 1 to calculate the fluorescence lifetime.

An alternative application of the embodiment of FIG. 4 includes a frequency feedback signal 154 which passes from the frequency and phase calculator 102 for varying the output of the frequency generators 82 and 96. In this manner, the frequencies of the signals 16, 26 and 84, and the phase of the signal 106 may also be simultaneously varied as in the embodiment illustrated in FIG. 2. Another alternative embodiment of FIG. 4 includes a digital signal processor 98 which contains an internal frequency generator 96 and digital to analog converter 140.

Referring now to FIG. 5, this embodiment is similar to that shown in FIG. 4 except that it lacks a means for downconversion of high frequency signal to lower frequencies for quadrature phase detection. Referring to FIG. 5, the down conversion arrangement of FIG. 4 has been eliminated. This FIG. 5 embodiment is particularly useful when only a single phase digital waveform generator is available in place of a dual-phase output digital waveform generator. In one implementation of this embodiment as illustrated in FIG. 5, the frequency generator 96 is a specialized DSP component that is external to the main digital signal processor 98 and contains a digital to analog converter 142. In another implementation, the frequency generator 96 is internal to the main DSP 98, as shown for example in FIGS. 1 and 2.

In this embodiment, as in the prior embodiment, the experimental signal 16 and the reference signal 26 are generated by one single-output frequency generator 96 and are generated at substantially the same phase and frequency. As in prior embodiments, the experimental signal 16 passes through the light source 22, the luminescent sample 32, and the photodetector 36. The signal 38 output from the photodetector 36 is converted to a voltage at the preamplifier 40 and filtered at the anti-aliasing filter 42 as in prior embodiments. The experimental output signal 38 is then digitized at the analog-to-digital converter 48. The reference input signal 26 also passes through a substantially identical anti-aliasing filter 44 and is digitized at the analog-to-digital converter 50. The digitized representations of the experimental output signal 38 and the reference signal 26 are digital experimental signal 94 and digital reference signal 92, respectively.

As in the prior embodiment of FIG. 4, when the signals 92 and 94 pass through the analog-to-digital converters 50, and 48, they are not mixed directly together. Instead, an additional dual-output, multiphase digital synthesis frequency generator 100 is provided within the DSP 98. As in the prior FIG. 4 embodiment, this generator 100 allows both the digital experimental signal 94 and the digital reference signal 92 to be compared in quadrature at two different digital mixers, 108 and 110.

As in the previously described embodiment of FIG. 4 and in preferred form, the dual-output, multi-phase digital synthesis frequency generator 100 includes a frequency and phase calculator 102 that generates a first internal signal 104 and a second internal signal 106, each of which has a frequency which matches substantially exactly the frequency of the signals 92 and 94, which is the difference frequency between the frequency generated by the generator 96 and the frequency generated by the generator 82. The signal 104 is generated such that it has a phase of 90° relative to the input signal 92. This is accomplished by mixing the signals 92 and 104 at a mixer 108. The output of the mixer 108 is directed to a low pass filter 150 which outputs error signal 152, the sign and magnitude of which indicates the relative phase difference between signals 104 and 92. The error signal 152, preferably zero when the signals 92 and 104 are in quadrature, is directed to the frequency and phase calculator 102. The calculator 102 adjusts the phase of signal 104 until the error signal 152 indicates that signals 92 and 104 are in quadrature.

At the same time, the signal 94 is directed toward a mixer 110, and generator 100 generates signal 106 of preferably identical frequency with signals 92, 94 and 104, and with phase that is advanced a known amount with respect to the phase of signal 104. The signal 106 is mixed with the signal 94 at the mixer 110, the output of which is directed through the low pass filter 56 to create the error signal 114 which is directed to the frequency and phase calculator 102. Based on the sign and magnitude of the error signal 114, the phase of the signal 106 is shifted until the signal 106 and the signal 94 are in quadrature at the mixer 110. Since the signals 92 and 94 preferably differ in phase only based on the phase shift caused by the target sample 32, each of the signals 92 and 94 are individually placed into quadrature with separate signals in order to determine this difference in phase at the synthesis frequency generator 100. The phase difference between signals 104 and 106 thus reflects the phase difference between the input signals 92 and 94. The fluorescence lifetime of the sample can be calculated using the measured phase shift, frequency with Equation 1.

As with the prior embodiment, the additional phase locked loop made up of the generator 100, the feedback signal 152, the mixer 108 and the integrator 150 allows an additional known amount phase shift to be added to internal reference signal 106 so that the digitized experimental can be compared in quadrature to a signal of known phase.

An alternative application of the embodiment of FIG. 5 includes the frequency feedback signal 154 which passes from the frequency and phase calculator 102 for varying the output frequency of the generator 96. In this manner, the frequencies of the signals 16 and 26, and the phase of signal 106 may also be simultaneously varied as in the embodiment illustrated in FIG. 2.

Referring now to FIG. 6, this embodiment describes a device 12 that uses a Digital Signal Processor 200 for measuring phase shifts of an analog signal 202 through a phase shifting element 204, relative to the phase shifts of an analog signal 206 of substantially identical frequency through a reference element 208. In a preferred embodiment, the analog signals 202 and 206 are sinusoidal and substantially identical in frequency. The signals 202 and 206 are preferably generated by a dual-output, variable phase and frequency waveform generator 210, which is contained in the DSP 200. The digital outputs, 212 and 214, of the waveform generator 210 are directed to digital-to-analog converters 216 and 218. The digital-to-analog converters output analog signals 202 and 206 which are directed to the phase shifting element 204 and the reference element 208, respectively.

In the preferred embodiment of this FIG. 6, the phase shifting element 204 contains a fluorescent material that changes lifetime in response to some analyte. Additionally, the phase shifting element 204 may also contain an excitation light source, a photodetector, a pre-amplifier, and anti-aliasing filters as described in the previous embodiments. The reference element 208 preferably contains substantially identical anti-aliasing filters which add substantially the same amount of phase shift to the signal as the anti-aliasing filters of the phase shifting element, as explained in the previous embodiments. It should be noted that the phase shifting element does not necessarily contain a fluorescent sample. It may, in fact, consist of many types of electrical or optical phase shifting components.

The output signal 220 of the phase shifting element 204, and the output signal 222 of the reference element 208 are directed then towards analog-to-digital converters 224 and 226, respectively. The analog to digital converters 224 and 226 convert the analog signals 220 and 222 into digital representations in the DSP 200. The digitized signals 220 and 222 are then directed towards a digital phase demodulator 228. In the preferred embodiment of this FIG. 6, the DSP 200 contains a digital phase demodulator 228, a low pass filter 230, a dual-output variable-phase waveform generator 210, and a filtered feedback error signal 232 from the phase demodulator 228. As described in previous embodiments, these elements act in concert to force the digital signals 220 and 222 into quadrature at the digital phase demodulator 228. Under conditions of quadrature, the phase shift between the two signals 220 and 222 due to the phase shifting element 204 can be determined using one of the methods of the previous embodiments.

This FIG. 6 embodiment of the invention preferably includes a single analog timing element 234, which provides a master timing base for all digital signal generation and phase comparison operations in the DSP 200. In the preferred embodiment, the timing element 234 consists of a quartz crystal oscillator. The timing element 234 generates a high frequency clock signal 236 that is directed to a clock divider 238. In one preferred embodiment, the high frequency clock signal 236 is approximately 25 MHz. The clock divider 238 then digitally divides the clock signal 236 into a lower frequency clock signal 240. This lower frequency clock signal 240 becomes the timing signal for all operations relating to the determination of the relative phase between signals 220 and 222. In the preferred embodiment, the frequency of the clock signal 240 is substantially 48 kHz. Depending on the specific components used, the clock signal 240 may differ significantly from 48 kHz.

The clock signal 240 is preferably directed to the digital-to-analog converters 216 and 218 and the analog-to-digital converters 224 and 226. At the digital-to-analog converters 216 and 218, the clock signal 240 causes the conversion of a pair of digital points representing waveforms 212 and 214 to analog signals 202 and 206. Simultaneously, the clock signal 240 causes the analog-to-digital converters 224 and 226 to convert the incoming analog signals 220 and 222 into a pair of digital points representing the analog signals 220 and 222. Since the analog signal generation and digitization are synchronized to the clock signal 240, these events occur simultaneously and with essentially no phase jitter.

The clock signal 240 additionally causes the phase demodulator 228, the filter 230 and the waveform generator 210 to perform calculations on the next set of digital numbers 220 and 222. When the analog signals 220 and 222 are digitized, their digital representations are first directed to a digital phase demodulator 228. The result of the digital phase demodulator 228 is directed to a digital filter 230, which outputs a filtered error signal 232 which is then directed to the waveform generator 210. The waveform generator 210 then generates a new set of digital numbers for digital signals 212 and 214. The phase and frequency of the digital signals 212 and 214 are determined by the value of the error signal 232. At every cycle of the clock signal 240, the above operations are performed once and the operations are completed before the next cycle of clock signal 240. The waveform generator 210 also provides for a means that the frequency and relative phase of signals 212 and 214 can be output at each cycle of clock signal 240. Thus, at each cycle of the clock signal 240, the lifetime of the phase shifting element 204 can be determined essentially continuously using Equation 1.

In the preferred embodiment of FIG. 6, the clock divider 238, the digital-to-analog converters 216 and 218 and the analog-to-digital converters 224 and 226 are contained in a integrated circuit separate from the DSP 200, while the waveform generator 210 is contained within the integrated circuit of the DSP. It should be understood that these components may be contained either within or outside of the DSP 200 without departing from the spirit of the invention. Moreover, the frequencies of the signals 212 and 214 are substantially the same as the frequencies of signals 220 and 222. It should also be further understood that the phase shifting element 204 and the reference element 208 can include a means for downconverting, as previously described, from the input frequencies 202 and 206 to lower frequencies for signals 220 and 222 without departing from the spirit of the invention.

In order to better understand how various of the embodiments of the present invention operate, the following examples are provided. It should be understood, however, that these examples are only for purposes of illustration and are not intended to limit the scope of the invention which is defined by the claims appended hereto.

EXAMPLE I

The device 10 of FIG. 1 was implemented using a commercially available ADSP2181 EZLAB prototyping kit from Analog devices and additional analog components as described below. The DSP 12 consisted of an Analog Devices ADSP-2181 KS-133. Dual output waveform generator 14 was implemented in software using Direct Digital Synthesis, a commonly used method for generating digital waveforms (see description in Analog Devices technical specifications for part#AD9830, Rev. A, p. 10). The two digital output signals 16 and 26 were directed to a ΔΣ Stereo (2 channel) CODEC (Analog Devices part #AD1847JP) which generated two 20 KHz counterpart analog sine-waves with a relative phase difference as specified by the waveform generator 14. The CODEC output each analog signal with an sampling rate of 48 KHz.

One 20 KHz sine wave 16 was directed to an operational amplifier (Analog Devices AD810) that provided sinusoidal current drive to the LED 22. The light output of the blue LED (Nichia NSPB500S) was immediately filtered using a blue-interference filter that blocked the longer wavelength light (yellow, orange and red) produced by the LED. The resulting blue light, 30, was directed towards a sample 32.

The sample 32 used in this example and embodiment consisted of platinum-tetrapentafluorophenyl porphyrin (PtTFPP) dispersed in a proprietary oxygen permeable matrix. This sample had a luminescent lifetime of 18.5 microseconds at ambient temperature and pressure. The red luminescence of the sample 34 was directed towards a photodiode 36 having a red interference filter to remove any scattered blue excitation light 30. The output current 38 of the photodiode 36 (Hamamatsu PIN photodiode S4707-01), was directed towards a transimpedance amplifier 40 (Burr Brown OPA655) with gain which converted the sinusoidally varying photodiode output current into a sinusoidally varying voltage. The voltage signal 38 was directed to an anti-aliasing filter 42. The anti-aliasing filters 44 and 42 consisted of single-section, low-pass RC filters with time constants of 3.3 $\mu$sec. The output of the anti aliasing filter 42 was directed towards the input side 48 of the Stereo CODEC where the signal was sampled and digitized at a rate of 48 KHz.

The analog reference signal 26 was directed to an anti-aliasing filter 44, which consisted of essentially the same components as the anti-aliasing filter 42 in the signal path as described above. The filtered reference signal 46 was directed to the second input 50 of the CODEC and digitized at a rate of 48 KHz, synchronously with the sample analog signal 38.

The digitized representations of the signals 46 and 38 were multiplied point by point at a rate of 48 KHz at phase demodulator 52. The phase demodulator 52, implemented in software, multiplied the digitized data pairs of the time series generated by the CODEC 48, 50. The result of the phase demodulator 52 was sent to a low pass filter 56. The low pass filter 56 consisted of a digital IIR single or double pole low pass filter implemented in the ADSP2181 (see Oppenheim, A. V., and R. W. Schafer. *Discrete-Time Signal Processing*. Englewood Cliffs, N.J.: Prentice-Hall, 1989.)

The output 58 of this filter 56, which represents the sign and magnitude of the phase difference between the signals 46 and 38, was directed to the dual output waveform generator 14. The error signal 58 causes the waveform generator 14 to change the phase advance of the reference signal 26 to a value which puts the signals 46 and 38 in quadrature at the phase demodulator 52. This condition is met when the error signal is zero.

Using the sample described above at ambient temperature and pressure, and 20 KHz excitation, the sample produced a phase shift of −21.9°. Several other elements contribute phase shift equally to both the sample channel and the reference channel, (e.g. the CODEC and the anti-aliasing filters) and did not change the relative phase of the two signals. Since there was a −21.9° phase shift though the luminescent sample, the dual output waveform generator 14 adjusted the phase advance of reference signal 26 to 68.1° to achieve quadrature conditions at the phase demodulator 52. The phase shift of the sample was determined by computing the difference between 90° (quadrature) and the phase advance added to the reference channel, 68.1°, or in other words 90°−68.1°=21.9°. The lifetime of the sample 32 was calculated using Equation 1 above.

EXAMPLE II

The device 10 of FIG. 2 was implemented using a commercially available ADSP2181 EZLAB prototyping kit from Analog devices and additional analog components as described below. The DSP 60 consisted of an Analog Devices ADSP-2181 KS-133. Dual output waveform generator 14 was implemented in software using Direct Digital Synthesis as in Example I. The two digital output signals 16 and 26 were directed to a $\Delta\Sigma$ Stereo (2 channel) CODEC (Analog Devices part #AD1847JP) which produced two counterpart analog sine-waves with a relative phase difference and frequency as specified by the waveform generator 14. For any frequency and phase relationship, the CODEC output the analog signal using a sampling rate of 48 KHz.

One sine wave 16 was directed to an operational amplifier (Analog Devices AD810) that provided sinusoidal current drive to the LED 22. The light output of the blue LED (Nichia NSPB500S) was immediately filtered using a blue-interference filter that blocked the longer wavelength light (yellow, orange and red) produced by the LED. The resulting blue light 30 was directed towards a sample 32. The sample 32 used in this Example II was similar to that of Example I and consisted of platinum-tetrapentafluorophenyl porphyrin (PtTFPP) dispersed in a proprietary oxygen permeable matrix. However, this sample had a luminescent lifetime of 7.27 microseconds at 100% oxygen at ~760 Torr and 45° C.

The red luminescence 34 of the sample 32 was directed towards a photodiode 36 (Hamamatsu PIN photodiode S4707-01) having a red interference filter to remove any scattered blue excitation light 30. The output current of the photodiode 36 was directed towards a transimpedance amplifier 40 (Burr Brown OPA655) with gain which converted the sinusoidally varying photodiode output current into a sinusoidally varying voltage. The voltage signal 38 was directed to an anti aliasing filter 42. The anti-aliasing filters 44 and 42 consisted of single-section, low-pass RC filters with time constants of 3.3 $\mu$sec. The output of the anti-aliasing filter 42 was directed towards the input side 48 of the Stereo CODEC where the signal was sampled and digitized at a rate of 48 KHz.

The analog reference signal 26 was directed to an anti-aliasing filter 44 which consisted of essentially the same components as the anti-aliasing filter 42 in the signal 38 path. The filtered reference signal 46 was directed to the second input 50 of the CODEC and digitized at a rate of 48 KHz synchronously with the sample analog signal 38.

The digitized representations of the signals 46 and 38 were multiplied point by point at a rate of 48 KHz at the phase demodulator 52. The phase demodulator 52, implemented in software, multiplied the digitized data pairs of the time series generated by the CODEC. The resulting signal 54 of the phase demodulator 52 was sent to a low pass filter 56. The low pass filter consisted of a digital IIR single or double pole low pass filter implemented in the ADSP2181 as previously mentioned for Example I. The output signal 58 of this filter 56, which represents the sign and magnitude of the phase difference between signals 46 and 38, was directed to the dual output waveform generator 14. The error signal 58 caused the waveform generator 14 to simultaneously and continuously change the phase advance of the reference signal 26 and the frequency of signals 16 and 26 to values which puts the signals 46 and 38 in quadrature at the phase demodulator 52. This condition is met when the error signal is zero.

Using the sample 32 described above in 100% oxygen at 760 Torr and 45° C., a 15.940 kHz excitation and phase offset of 53.904° were required to achieve conditions of quadrature at the mixer 52. Several other elements contributed phase shift equally to both the sample channel and the reference channel, (e.g. the CODEC, and the anti-aliasing filters) and thus did not change the relative phase of the two signals. As previously described, the dual output waveform generator 14 contains a frequency calculator and phase calculator 64 which determines the phase advance of signal 26 and the frequency of signals 16 and 26 based on the feedback error signal 58. The frequency and phase calculator were set to adjust the phase and frequency according to the following equation:

$$N°=0.0038\ F+6.18 \qquad \text{Equation (3)}$$

The phase advance of the signal 26, that is N°, and the frequency F of the signals 16 and 26 at any particular phase advance, N°, were determined by Equation 3. The waveform generator 62 increased or decreased N°, and hence simultaneously lowered or raised the frequency F according to Equation 3, until the error signal indicated that the inputs 38 and 46 to the phase demodulator 52 were in quadrature.

Since there is a −36.096° phase shift though the luminescent sample, the dual output waveform generator adjusted the phase advance of reference signal 26 to 53.904° to achieve quadrature conditions at the phase demodulator 52. Following Equation 3, the frequency was set to 15.94 kHz. The phase shift of the sample was determined by computing the difference between the phase advance added to the reference channel, 53.904°, and 90° (quadrature), or 53.904°−90°=−36.096°. The lifetime of the sample then was calculated using Equation 1 above.

EXAMPLE III

The device 10 of FIG. 3 is implemented using a commercially available ADSP2181 EZLAB prototyping kit from Analog devices and additional analog components as described below. The DSP 60 consists of an Analog Devices ADSP-2181 KS-133. Dual output waveform generator 62 is implemented in software using Direct Digital Synthesis as previously mentioned in the Examples I and II, or if the output frequencies required are too high for generation in software, the waveform generator is implemented externally in a custom DSP chip and clocked by the same master analog clock as the other digital components. The waveform generator 62 generates two digital output signals 16 and 26 that are then directed to an appropriate digital-to-analog converter 20 which produces two counterpart analog sine-waves with a relative phase difference and frequency as specified by the waveform generator 62.

As in the previous examples, one sine wave 16 is directed to an operational amplifier (Analog Devices AD810) to provide sinusoidal current drive to the LED 22. The light output of a blue LED (Nichia NSPB500S) is immediately filtered using a blue-interference filter that blocks the longer wavelength light (yellow, orange and red) produced by the LED. The resulting blue light 30 is then directed towards a sample 32. The sample 32 consists of a fluorescent sample the lifetime of which is quenched in the presence of the analyte of interest. The lifetime of the sample can be quite short, for example 0.5 nsec to 5 nsec. At 10 MHz excitation, a fluorescent sample with a 5 nsec lifetime exhibits a phase shift of 17°.

The longer wavelength fluorescence of the sample 34 is directed towards a photodetector 36, such as a photomultiplier tube, avalanche photodiode or other appropriate detector, having an appropriate interference filter to remove any scattered blue excitation light 30. The output current 38 of the photodetector 36 is directed towards a transimpedance amplifier 40 (e.g. Burr Brown OPA655) to convert the sinusoidally varying photodetector output current into a sinusoidally varying voltage 38. The voltage signal 38 is then directed to an analog mixer 90. The analog reference signal 26 is also directed to similar analog mixer 88.

This embodiment provides for a second waveform generator 82, which in this example is a commercially available AD9830. This waveform generator 82 outputs a high frequency digital signal 84 which is then converted into an analog signal at an appropriate digital-to-analog converter 86 as previously described. The digital-to-analog converter 86 may in fact be integral to the second waveform generator 82. The second waveform generator 82 outputs a signal 84 with a frequency that is a constant difference from the frequencies of signals 16 and 26. For example, if the signals 16 and 26 are 10 MHz signals, the second waveform generator 82 outputs a signal of 10.02 MHz. In this example, the constant difference between the first generator 62 and second generator 82 is 20 KHz. If the output frequency of the waveform generator 62 changes, the output of the second generator 82 tracks the output frequency of the first generator 62 such that the difference in frequencies remains 20 kHz.

The analog output 84 of the second generator is split into two identical signals directed towards the analog mixers 88 and 90. Both analog mixers 88 and 90 perform substantially identically, their outputs being a linear multiplication of the two input signals. These outputs 92 and 94 contain the sum and difference frequencies of the input signals to the respective mixers 88 and 90. In this example, the mixer output thus consists of a 20.02 MHz signal and a 20 kHz signal.

The sum and difference frequency outputs of the analog mixers 88 and 90 are filtered at similar anti-aliasing filters 44 and 42. These anti-aliasing filters 44, 42 are configured so that the sum frequencies, 20.02 MHz, are removed, leaving only the difference frequencies, i.e. 20 kHz. As described above, the downconverted 20 kHz difference frequencies carry the same relative phase information as did the 10 MHz signals that passed through the fluorescent sample and the reference path. Appropriate anti-aliasing filters are, for example, single-section, low-pass RC filters with time constants of 3.3 μsec.

The output signal of each of the anti-aliasing filters 42 and 44 is directed towards the input of an analog-to-digital converter 48, 50, respectively, where the signal is sampled and digitized at an appropriate rate, e.g. 48 KHz. The digitized representations of filtered signals 92 and 94 are then multiplied point by point at a rate of 48 KHz at the phase demodulator 52. The phase demodulator 52, implemented in software, multiplies the digitized data pairs of the time series generated by the analog-to-digital converter. The resulting signal 54 of the phase demodulator 52 is sent to a low pass filter 56. The low pass filter consists of a digital IIR single or double pole low pass filter implemented in the ADSP2181 as previously mentioned.

The output signal 58 of this filter 56, which represents the sign and magnitude of the phase difference between filtered signals 92 and 94, is directed to the high-frequency dual-output waveform generator 62 as well as the second high frequency generator 82. The error signal 58 causes the waveform generator 62 to simultaneously and continuously change the phase advance of the reference signal 26 and the frequency of signals 16 and 26 to values which puts the filtered signals 92 and 94 in quadrature at the phase demodulator 52. This condition is met when the error signal is zero.

The dual output waveform generator 62 can be operated in one of two modes. It can be operated in a first mode at a constant frequency and variable phase shift, as in Example I, or it can be operated in a second mode simultaneously at a continuously variable frequency and phase with compression, as in Example II. If the waveform generator 62 is operated in the second mode, the error signal 58 also acts on the second high frequency generator 82 to adjust its frequency so that it is at a constant 20 kHz difference from the frequency output of the first generator 62. The sample lifetime is calculated as in Examples I and II using the phase shift and frequency with Equation 1.

EXAMPLE IV

The device 10 of FIG. 4 was implemented using a commercially available ADSP2181 EZLAB prototyping kit from Analog devices and additional analog components as described below. The DSP 98 consisted of an Analog Devices ADSP-2181 KS-133. Unless stated otherwise, the components of this Example IV were the same specific components utilized in the previous examples. Instead of the dual-output waveform generator described in the Example III above, a single-output Direct Digital Synthesis waveform generator 96 was used to generate a high frequency sinusoid that drove an LED 22 to generate blue light for excitation of the sample. The waveform generator 98 consisted of an Analog Devices EVAL-AD9830EB which contained an analog Devices AS9830 Direct Digital Synthesis IC.

The waveform generator 96 contained an internal analog-to-digital converter 142 and output a sine wave of a known frequency, i.e. 1.013 MHz. This sine wave output was split into two identical signals 16 and 26. One signal 16 was directed towards an operational amplifier, Analog Devices AD811, which provided sinusoidal current drive to a blue LED 22 (Nichia NSPB500S), and the other signal, the analog reference signal 26, was sent to an analog mixer 88.

The light output of a blue LED 22 (Nichia NSPB500S) was immediately filtered using a blue-interference filter that blocked the longer wavelength light (yellow, orange and red) produced by the LED. The resulting blue light 30 was directed towards a sample 32. The sample 32 consisted of a dilute fluorescent sample in a buffer of pH 7.6. The lifetime of the sample was 4 nsec under ambient conditions.

The longer wavelength luminescence of the sample 34 was directed towards a photomultiplier tube 36 (Hamamatsu R5600U-01) which had a 600 nm longpass filter to remove any scattered blue excitation light 30. The output current 38 of the photomultiplier tube 36 was directed towards a transimpedance amplifier 40 (e.g. Burr Brown OPA655) to convert the sinusoidally varying photodetector output current into a sinusoidally varying voltage. The voltage signal 38 was directed to an analog mixer 90. The analog reference signal 26 was directed to a similar analog mixer 88.

This device 10 had a second waveform generator 82, which consisted of a Analog Devices EVAL-AD9830EB containing an analog Devices AS9830 Direct Digital Synthesis IC. This second waveform generator 82 output a high frequency analog signal 84 that was a constant difference from the frequencies of signals 16 and 26. In this example the second oscillator frequency was 1.0078 MHz, a constant difference from the first oscillator frequency of 5.2 kHz. The analog output 84 of the second generator 82 was split into two identical signals directed towards the analog mixers 88 and 90. Both analog mixers 88, 90 acted substantially identically in that the output of each was a linear multiplication of their two respective input signals, i.e. signals 26 and 84 for the mixer 88 and signals 38 and 84 for the mixer 90. These outputs 92 and 94 contained the sum and difference frequencies of the input signals. In this example, the mixer output consisted of a 2.0208 MHz signal and a 5.2 kHz signal.

The sum and difference frequency outputs of the analog mixers 88, 90 were filtered at similar anti-aliasing filters 44 and 42. These anti-aliasing filters were configured so that the sum frequencies, 2.0208 MHz, were removed, and the difference frequencies, i.e. 5.2 kHz, were passed on. As described above, the downconverted 5.2 kHz difference frequencies carried the same relative phase information as did the 1.013 MHz signals 16, 26 that passed through the luminescent sample 32 and that acted as the analog reference signal, respectively. Single-section, low-pass RC filters with time constants of 3.3 $\mu$sec were used to filter the downconverted signals.

The output of the anti-aliasing filters 44 and 42 were directed to the inputs 50, 48 of a $\Delta\Sigma$ Stereo (2 channel) CODEC (Analog Devices part #AD1847JP) where the signals were digitized at a rate of 48 KHz. The digitized filtered reference signal 92 was directed to a digital phase demodulator 108. A second input to the digital phase demodulator was a 5.2 kHz digital sine wave 104, generated by an internal dual-output waveform generator 100. The digital phase demodulator 108 consisted of a point by point multiplication which operated at 48 kHz, which is the rate of digitization of the CODEC.

The error signal generated by this phase demodulator 108 was then filtered with a digital IIR single or double pole low pass filter 150 implemented in the ADSP2181 as previously mentioned. The filtered error signal 152 was input to the dual-output waveform generator 100, which adjusted the phase of the digital sine wave 104 such that it was in quadrature with the digitized reference signal 92 at the demodulator 108. Because the reference signal 92 has an unknown phase of α, as noted in FIG. 4, the digital phase lock loop described above locks one output, 104, of the internal dual-output waveform generator to the digitized reference input, signal 92. Specifically, the action of the mixer 108 and the feedback error signal 152 causes signal 104 to have a phase shift 90° advanced with respect to the signal 92, or α+90°.

The 5.2 kHz downconverted digitized signal from the fluorescence experiment, signal 94, was directed towards a second digital phase demodulator 110 in the DSP. The second input to this phase demodulator was the second output 106 of the internal dual-output waveform generator 100. As with the other digital phase demodulator 108, the result of the point-by-point multiplication passes through a IIR single or double pole low pass digital filter 56. This filtered signal 114, the error signal of the phase demodulator 110, was directed towards the phase and frequency calculator 102 of the internal dual-output waveform generator 100. The phase and frequency calculator 102 caused the waveform generator 100 to output a signal 106 at 5.2 kHz with a phase 90° advanced with respect to the digitized signal from the fluorescence experiment, signal 94.

Because both signals 104 and 106 generated by the internal dual-output waveform generator 100 are in quadrature with the downconverted digitized reference and fluorescence experiment signals 92 and 94, respectively, the phase difference between the two signals generated by the internal dual-output waveform generator 100 reflect the phase difference between the digitized reference and fluorescence experiment signals 92, 94. Thus, the total phase delay resulting from the contribution of the excitation light source, the fluorescence experiment, the photodetector and the transimpedance amplifier are known. Since the phase delay added by the fluorescence experiment 32 is the parameter of interest, the phase delays due to other components of the system were factored out by measuring a fluorescence sample of known lifetime.

In this particular example, the phase delays of the excitation light source, fluorescent sample (fluorescein), the photodetector and the pre-amplifier amounted to −13.42°. This was measured by determining the difference between the two digital output signals 104, 106 of the internal dual-output waveform generator 100, while both of the phase demodulators 108, 110 in the DSP were operating in quadrature. Of the −13.42° phase shift, −1.46° were due to the 4 ns lifetime of the fluorescent sample, and −11.96° resulted from phase shift in the excitation, photodetector and trans-impedance amplifier. The non-fluorescence sample phase shifts of −11.96° were assumed to be constant and thus subtracted from the measured phase difference between the downconverted signals 92 and 94. Equation 1 was used with θ=1.46°, and f=1.013 MHz to calculate the fluorescence lifetime of the sample.

As can be seen from the above, it is clear that the present invention provides a simple and effective apparatus and method for measuring environmentally and medically important analytes. The present invention accomplishes this by providing a unique apparatus and method for measuring time delay in samples targeted by electromagnetic radiation and in particular fluorescence emissions. The present invention provides a fluorescence-based sensing instrument and method applicable to a broad range of materials involving exponential decay and time delay measurements, and which is made from inexpensive components. While analog systems of the present art are subject to drift and therefore unnecessary errors, and the digital systems of the present art contain complex, expensive hardware, the present invention has been designed to avoid these problems. Consequently, the system of the invention is inexpensive, convenient to use and operates over an extended and continuous measurement range. In addition, the measurement approach of the device and method of the invention is susceptible to convenient and precise readout.

The foregoing description and the illustrative embodiments of the present invention have been described in detail in varying modifications and alternate embodiments. It should be understood, however, that the foregoing description of the present invention is exemplary only, and that the scope of the present invention is to be limited to the claims as interpreted in view of the prior art. Moreover, the invention illustratively disclosed herein suitably may be practiced in the absence of any element which is not specifically disclosed herein.

I claim:

1. An apparatus to measure emission time delay during irradiation of targeted samples by utilizing digital signal processing to determine the emission phase shift caused by the sample, said apparatus comprising:
   a source of electromagnetic radiation adapted to irradiate a target sample;
   means for generating first and second digital input signals of known frequencies with a known phase relationship;
   means for converting said first and second digital input signals to analog sinusoidal signals;
   means for directing said first analog input signal to said electromagnetic radiation source to modulate said electromagnetic radiation source by the frequency thereof to irradiate said target sample and generate a target sample emission;
   means for detecting said target sample emission and producing a corresponding first analog output signal having a phase shift relative to the phase of said first analog input signal, said phase shift being caused by the emission time delay in said sample;
   means for producing a known phase shift in said second analog input signal to create a second analog output signal;
   means for converting said first and second analog output signals to first and second digital output signals respectively;
   a mixer for receiving said first and second digital output signals and comparing the signal phase relationship therebetween to produce a signal indicative of the change in phase relationship between said first and second digital output signals caused by said target sample emission; and
   feedback means to simultaneously alter the frequencies of said first and second digital input signals while substantially continuously vary the phase offset between said first and second digital input signals based on said mixer signal to ultimately place said first and second digital output signals in quadrature while compressing the frequency range therebetween.

2. The apparatus as claimed in claim 1, wherein said signal generation means comprises a multiphase oscillator adapted to generate said input signals at specified frequencies and specified phases in response to said mixer signal.

3. The apparatus as claimed in claim 2, wherein said feedback means comprises a long pass filter for extracting and amplifying said mixer signal, and wherein said multiphase oscillator includes a frequency calculator for adjusting frequency of said input signals and a phase calculator for adjusting the relative phase said variable input signals.

4. The apparatus as claimed in claim 3, wherein said mixer includes means for filtering out the sum frequency of the first output and third input signals and the sum frequency of the second output and third input signals so that said analog-to-digital conversion means digitizes only the said difference frequencies of the output signals and said mixer compares the phase of only the difference frequency between the first output and third input signals with the difference frequency between the second output and third input signals.

5. The apparatus as claimed in claim 4, wherein said apparatus further comprises means for generating a fourth digital signal having a frequency the same as said second output signal, means for mixing said second digital output signal with said fourth digital signal to create a feedback signal to said fourth signal generation means to adjust the phase of said fourth digital signal until it is in quadrature with said second digital output signal, means for generating a fifth digital signal having a frequency substantially the same as said fourth digital signal, means for mixing said fifth digital signal with said first digital output signal and generating an adjustment output signal therefrom, and means for varying the phase of said fifth digital signal based on said adjustment output signal to place said fifth digital signal and said first digital output signal in quadrature to determine the phase shift caused by the emission time delay of said targeted sample.

6. The apparatus as claimed in claim 5, wherein said signal generation means comprises a multiphase oscillator having a frequency calculator adapted to generate and adjust the frequencies of said first and second input signals and a phase calculator to adjust the phase of said second input signal in response to said mixer signal, and a second signal generation means to create said third input signal frequency, and wherein said feedback means comprises a low pass filter for extracting and amplifying said mixer signal and a second frequency calculator for adjusting the output of said second signal generation means.

7. The apparatus as claimed in claim 1, wherein said mixer comprises a phase demodulator, and said feedback means includes a low pass filter for extracting and amplifying said phase demodulator signal and a phase calculator for adjusting the phase of said second digital signal to ultimately place said first and second output signals in quadrature.

8. The apparatus as claimed in claim 1, wherein said targeted sample comprises a fluorescent sample exposed to a light source modulated by said first input signal to cause said sample to generate fluorescence emissions having said phase shift.

9. The apparatus as claimed in claim 1, wherein said targeted sample comprises turbid media exposed to a light source modulated by said first input signal to cause said sample to emit time delayed scattered radiation having said phase shift.

10. An apparatus to measure emission time delay during irradiation of targeted samples by utilizing digital signal processing to determine the emission phase shift caused by the sample, said apparatus comprising:

a source of electromagnetic radiation adapted to irradiate a target sample;

means for generating first and second digital input signals of known frequencies with a known phase offset;

means for converting said first and second digital input signals to analog sinusoidal signals;

means for directing said first analog input signal to said electromagnetic radiation source to modulate said electromagnetic radiation source by the frequency thereof to irradiate said target sample and generate a target sample emission;

means for detecting said target sample emission and producing a corresponding first analog output signal having a phase shift relative to the phase of said first analog input signal, said phase shift being caused by the emission time delay in said sample;

means for producing a known phase shift in said second analog input signal to create a second analog output signal;

means for converting said first and second analog output signals to first and second digital output signals respectively;

a mixer for receiving said first and second digital output signals and comparing the signal phase relationship therebetween to produce a signal indicative of the change in phase relationship between said first and second digital output signals caused by said target sample emission; and feedback means to simultaneously alter the frequencies of said first and second digital input signals while substantially continuously varying the phase offset between said first and second digital input signals based on said mixer signal to ultimately place said first and second digital output signals in quadrature while compressing the frequency range therebetween.

11. The apparatus as claimed in claim 10, wherein said apparatus further comprises means for directing said first and second output signals individually through an antialiasing filter prior to said analog-to-digital conversion means.

12. The apparatus as claimed in claim 10, wherein said signal generation means comprises a multiphase oscillator adapted to generate said input signals at specified frequencies and to adjust the relative phase of said generated input signals in response to said mixer signal.

13. The apparatus as claimed in claim 12, wherein said feedback means further comprises a phase calculator adapted to receive said mixer signal and determine relative phase of input signals and a frequency calculator adapted to receive said mixer signal and determine frequency of said input signals.

14. The apparatus as claimed in claim 10, wherein targeted sample comprises a fluorescent sample exposed to a light source modulated by said first input signal to cause said sample to generate fluorescence emissions having said phase shift.

15. The apparatus as claimed in claim 10, wherein said targeted sample comprises turbid media exposed to a light source modulated by said first input signal to cause said sample to emit time delayed scattered radiation having said phase shift.

16. The apparatus as claimed in claim 10, wherein said signal generation means is adapted to generate a third input signal, and wherein said apparatus further comprises a first signal down conversion means positioned for combining the frequency of said third input signal with the frequency of said first output signal to produce a modified first output signal representing the sum and difference frequencies of said first output and said third input signals, and a second signal down conversion means positioned for combining the frequency of said third input signal with the frequency of said second output signal to produce a modified second output signal representing the sum and difference frequencies of said second output and said third input signals, said analog-to-digital conversion means, converting said first and second modified output signals to digital signals for receipt by said mixer.

17. An apparatus to measure emission time delay during irradiation of targeted samples by utilizing digital signal processing to determine the emission phase shift caused by the sample, said apparatus comprising:

a source of electromagnetic radiation adapted to irradiate a target sample;

means for generating first, second and third digital input signals of known frequencies with known phase offsets;

means for converting said first, second and third digital input signals to analog sinusoidal signals;

means for directing said first analog input signal to said electromagnetic radiation source to modulate said electromagnetic radiation source by the frequency thereof to irradiate said target sample and generate a target sample emission;

means for detecting said target sample emission and producing a corresponding first analog intermediate signal having a phase shift relative to the phase of said first analog input signal, said phase shift being caused by the emission time delay in said sample;

first signal down conversion means for combining the frequency of said third analog input signal with the frequency of said first analog intermediate signal to produce a first analog output signal representing the sum and difference frequencies of said first analog intermediate and said third analog input signals;

means for producing a known phase shift in said second analog input signal to create a second analog intermediate signal;

second signal down conversion means for combining the frequency of said third analog input signal with the frequency of said second analog intermediate signal to produce a second analog output signal representing the sum and difference frequencies of said second analog intermediate and said third analog input signals;

means for converting said first and second analog output signals to first and second digital output signals, respectively;

a mixer for receiving said first and second digital output signals and comparing the signal phase relationship therebetween to produce a signal indicative of the change in phase relationship between said first and second digital output signals caused by said target sample emission; and feedback means to simultaneously alter the frequencies of said first and second digital input signals while substantially continuously varying the phase offset between said first and second digital input signals based on said mixer signal and to alter the frequency of said third digital input signal to achieve desired downconversion frequency of said first and second digital output signals to ultimately place said first and second digital output signals in quadrature while compressing the frequency range therebetween.

18. The apparatus as claimed in claim 17, wherein said mixer includes means for filtering out the sum frequency of said first intermediate and third input signals and the sum frequency of said second intermediate and third input signals to enable said analog-to-digital conversion means to digitize only the difference frequencies of said first and second output signals, said mixer comparing the phase of only the difference frequency between said first and second output signals.

19. The apparatus as claimed in claim 18, wherein said apparatus further comprises means for generating a fourth digital signal having a frequency the same as said second output signal, means for mixing said second digital output signal with said fourth digital signal to create a feedback signal to said fourth signal generation means to adjust the phase of said fourth digital signal until it is in quadrature with said second digital output signal, means for generating a fifth digital signal having a frequency substantially the same as said fourth digital signal, means for mixing said fifth digital signal with said first digital output signal and generating an adjustment output signal therefrom, and means for varying the phase of said fifth digital signal based on said adjustment output signal to place said fifth digital signal and said first digital output signal in quadrature to determine the phase shift caused by the emission time delay of said targeted sample.

20. The apparatus as claimed in claim 18, wherein said signal generation means is adapted to create said first and second input signals with substantially the same frequencies and said third input signal with a substantially different frequency.

21. A method for measuring emission time delay during the irradiation of targeted samples by utilizing digital signal processing for determining the emission phase shift caused by irradiation of the sample, said method comprising the steps of:

generating first and second digital input signals of known frequencies having a known variable phase relationship;

converting said first and second digital input signals to analog sinusoidal signals;

directing said first analog input signal to an electromagnetic radiation source to modulate the emissions of said electromagnetic radiation source by the frequency thereof;

irradiating a target sample with the modulated emissions of said electromagnetic radiation source to generate a target sample emission;

detecting said target sample emission and producing a corresponding first analog output signal having a phase shift relative to the phase of said first analog input signal, said phase shift being caused by the emission time delay of the emissions in said sample;

producing a known phase shift in said second analog input signal to create a second analog output signal;

converting said first and second analog output signals to first and second digital output signals, respectively;

mixing said first and second digital output signals and comparing the signal phase relationship therebetween to produce an error signal indicative of the change in phase relationship between said first and second digital output signals caused by said target sample emission; and altering the frequencies of said first and second digital input signals while continuously varying the phase offset between said first and second digital input signals to ultimately place said first and second digital output signals in quadrature while compressing the frequency range therebetween.

22. The method as claimed in claim 21, wherein said method further comprises the steps of generating a third input signal with said first and second input signals, down converting said first analog output signal by combining the frequency of said third input signal with the frequency of said first analog output signal to produce a modified first output signal representing the sum and difference frequencies between said first output and said third input signals, and down converting said second analog output signal by combining the frequency of said third input signal with the frequency of said second analog output signal to produce a modified second output signal representing the sum and difference frequencies between said second output and said third input signals, said first and second modified output signals being converted to digital signals.

23. The method as claimed in claim 22, wherein the sum frequency of the first output and third input signals and the sum frequency of the second output and third input signals are filtered out so that only the difference frequency between the first output and third input signals is mixed and phase compared with the difference frequency between the second output and third input signals.

24. The method as claimed in claim 22, wherein method further comprises the step of generating a fourth digital signal having a frequency the same as said second output signal, mixing said second digital output signal with said fourth digital signal to create a feedback signal to said fourth signal generation means to adjust the phase of said fourth digital signal until it is in quadrature with said second digital output signal, generating a fifth digital signal having a frequency substantially the same as said fourth digital signal, mixing said fifth digital signal with said first digital output signal to generate an adjustment output signal therefrom, and varying the phase of said fifth digital signal based on said adjustment output signal to place said fifth digital signal and said first digital output signal in quadrature to determine the phase shift caused by the irradiation of said targeted sample.

25. A method for measuring emission time delay during irradiation of targeted samples by utilizing digital signal processing to determine the emission phase shift caused by the sample, said method comprising the steps of:

generating first, second and third digital input signals of known frequencies with known phase offsets;

converting said first, second and third digital input signals to analog sinusoidal signals;

directing said first analog input signal to an electromagnetic radiation source to modulate said electromagnetic radiation source by the frequency thereof;

irradiating said target sample with the modulated emissions of said electromagnetic radiation source to generate a target sample emission;

detecting said target sample emission and producing a corresponding first analog intermediate signal having a phase shift relative to the phase of said first analog input signal, said phase shift being caused by the emission time delay in said sample;

down converting said first analog intermediate signal by combining the frequency of said third analog input signal with the frequency of said first analog intermediate signal to produce a first analog output signal representing the sum and difference frequencies of said first analog intermediate and said third analog input signals;

producing a known phase shift in said second analog input signal to create a second analog intermediate signal;

down converting said second analog intermediate signal by combining the frequency of said third analog input signal with the frequency of said second analog intermediate signal to produce a second analog output signal representing the sum and difference frequencies of said second analog intermediate and said third analog input signals;

converting said first and second analog output signals to first and second digital output signals, respectively;

mixing said first and second digital output signals and comparing the signal phase relationship therebetween to produce a mixer signal indicative of the change in phase relationship between said first and second digital output signals caused by said target sample emission; and simultaneously altering the frequencies of said first and second digital input signals while substantially continuously varying the phase offset between said first and second digital input signals based on said mixer signal and to alter the frequency of said third digital input signal to achieve desired downconversion frequency of said first and second analog and digital output signals to ultimately place said first and second digital output signals in quadrature while compressing the frequency range therebetween.

26. An apparatus to measure emission time delay during irradiation of targeted samples by utilizing digital signal processing to determine the emission phase shift caused by the sample, said apparatus comprising:

a source of electromagnetic radiation adapted to irradiate a target sample;

means for generating first, second and third digital input signals of known frequencies with a known phase relationship;

means for converting said first, second and third digital input signals to analog sinusoidal signals;

means for directing said first analog input signal to said electromagnetic radiation source to modulate said electromagnetic radiation source by the frequency thereof to irradiate said target sample and generate a target sample emission;

means for detecting said target sample emission and producing a corresponding first analog output signal having a phase shift relative to the phase of said first analog input signal, said phase shift being caused by the emission time delay in said sample;

means for producing a known phase shift in said second analog input signal to create a second analog output signal;

a first signal down conversion means positioned for combining the frequency of said third analog input signal with the frequency of said first analog output signal to produce a modified first analog output signal representing the sum and difference frequencies of said first analog output and said third analog input signals, and a second signal down conversion means positioned for combining the frequency of said third analog input signal with the frequency of said second analog output signal to produce a modified second analog output signal representing the sum and difference frequencies of said second analog output and said third analog input signals;

means for converting said first and second modified analog output signals to first and second digital output signals, respectively;

a mixer for receiving said first and second digital output signals and comparing the signal phase relationship therebetween to produce a signal indicative of the change in phase relationship between said first and second digital output signals caused by said target sample emission; and feedback means to alter the phase of the second digital input signal based on said mixer signal to ultimately place said first and second digital output signals in quadrature.

* * * * *